(12) United States Patent
Durfee et al.

(10) Patent No.: US 7,164,006 B1
(45) Date of Patent: Jan. 16, 2007

(54) ALTERATION OF PLANT MERISTEM FUNCTION BY MANIPULATION OF THE RETINOBLASTOMA-LIKE PLANT RRB GENE

(75) Inventors: Tim Durfee, Madison, WI (US); Heidi Feiler, Albany, CA (US); Wilhelm Gruissem, Forch (CH); Susan Jenkins, Martinez, CA (US); Judith Roe, Manhattan, KS (US); Patricia Zambryski, Berkeley, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 595 days.

(21) Appl. No.: 10/748,912

(22) Filed: Dec. 11, 2003

Related U.S. Application Data

(63) Continuation of application No. 09/527,084, filed on Mar. 16, 2000, now Pat. No. 6,696,560.

(60) Provisional application No. 60/125,229, filed on Mar. 19, 1999.

(51) Int. Cl.
*C07K 14/415* (2006.01)
(52) U.S. Cl. ...................................................... 530/370
(58) Field of Classification Search ..................... None
See application file for complete search history.

(56) References Cited

OTHER PUBLICATIONS

Xie et al. 1996, Genbank accession X98923.*

* cited by examiner

*Primary Examiner*—Ashwin Mehta
*Assistant Examiner*—Li Zheng
(74) *Attorney, Agent, or Firm*—Brian J. Lally; Daniel D. Park; Paul A. Gottlieb

(57) ABSTRACT

This invention provides methods and compositions for altering the growth, organization, and differentiation of plant tissues. The invention is based on the discovery that, in plants, genetically altering the levels of Retinoblastoma-related gene (RRB) activity produces dramatic effects on the growth, proliferation, organization, and differentiation of plant meristem.

1 Claim, No Drawings

SEQUENCE LISTING

<160> NUMBER OF SEQ ID NOS: 9

<210> SEQ ID NO 1
<211> LENGTH: 3474
<212> TYPE: DNA
<213> ORGANISM: Arabidopsis Thaliana

<400> SEQUENCE: 1

```
gaagtcaggt gaagatagag agagacactg agaggaggga aaatttgtag ggttttcgga        60
gatctctgtg attcctctga atttgtcgaa ttttttcgag gaggcgttag aagtcgggct       120
tcttaaaaat cagatcttct gctcaggctt taatcggcga cgtctggtat tgggatctgt       180
gacacaaaaa gctgcgttgg agactatgga agaagttcag cctccagtga ccccgcccat       240
tgaaccaaat gggaaaagaa gcgaagcctc tctcttggac atatgcgaga aagttctgtc       300
tcttgatggg agcacttgcg atgaagcttt gaagttgttt acagaaacca aacgaatttt       360
gtcagcaagc atgtctaaca ttggaagtgg aacgcgggaa gaagtagaga ggttctggtt       420
tgcgtttatt ctctattcag tgaagaggct tagtgtgaga aaagaagcgg atggtctgtc       480
agtgtctggt gataatgagt ttaatctatg tcagatactg agggctctga agctaaatat       540
tgtggatttt tttaaagagt tacctcagtt tgtggtcaag gctggatctg tactgggtga       600
actttacggc gcagactggg agaacagact tcaggcaaag gaggtgcagg ctaactttgt       660
gcatcttagc cttctaagca aatactacaa acgtgggttc cgggaattct ttttgacata       720
tgatgcaaac gcagaaaaga actcagcaaa ctcttctacc tatttgctgg atagttatcg       780
```

-continued

```
ttttggatgg ctactctttt tggcactccg aaaccatgcg tttagtcgat ttaaggacct      840
cgtgacatgc tcaaatggcg tagtttctat attggctatt ttgatcatac atgttccttg      900
tcggtttaga aatttcagca tccaagattc ttctcgcttt gttaagaaag gtgacaaagg      960
tgtagacttg gttgcatcac tttgcaagat atatgacgcc tcagaagatg agttgaggat     1020
agtaattgac aaggcaaata atttggtaga aaccatactg aagaaaaagc catctccagc     1080
atctgagtgc caaactgaca agctagataa tattgaccca gatggcttga cctactttga     1140
ggatttactg gaagagacgt ccatctcaac tagcttaatt acacttgaaa aggattacta     1200
tgatggtaaa ggcgaacttg atgagagggt attcatcaat gaagaggata gcttacttgg     1260
atctggaagc ttatctgcag gagctgttaa tattactggt gttaagagga aaattgatgc     1320
tttgagctca cctgcaagga catttataag cccactttct cctcataagt cgcctgctgc     1380
taagacaaat ggtattagcg gtgctaccaa gttggcagca acaccagtga gcacagcaat     1440
gacaactgcc aagtggctca ggactgtcat atccccgctt ctgccaaaac cttctcctgg     1500
gttggaacat ttccttaaat catgtgatag ggatataaca aatgacgtca cacgaagagc     1560
acacataata ttggaagcta ttttcccaaa tagttccctt ggtgcccaat gtggaggtgg     1620
aagtttgcaa gctgttgacc tgatggatga catatgggca gagcagcgca gattagaagc     1680
ttgtaagtta tactacagag ttcttgaggc aatgtgtaaa gcagaagctc agattttgca     1740
tgcaaataat ctgaactctt tattgacaaa tgagaggttc catagatgca tgcttgcttg     1800
ctcagctgaa ttggtactgg ctacccacaa aacaattaca atgttgttcc cagctgttct     1860
ggagaggact gggatcacag cctttgatct cagcaaggta attgagagtt tcatacgaca     1920
tgaagattct ctgcctagag agttgagacg acatctgaat tcactggagg aacggcttct     1980
agagagtatg gtatgggaga aggctcttc aatgtacaat tctctgattg ttgccaggcc     2040
atcgcttgca ttggagataa atcagctcgg tttactagct gaaccaatgc catctctgga     2100
tgcaatcgca gcacttatta atttctctga cggagcaaat catgcatcat ctgtacaaaa     2160
gcatgaaact tgtccaggac aaaatggggg gattagatcg cccaaaagat tatgtactga     2220
ttaccgcagc attctagttg aacgcaattc ctttacatca ccagtaaagg atcgtctgtt     2280
ggccttaggc aacgttaaat ccaagatgct gccacctccg ttgcagtctg catttgccag     2340
cccaacacgg cccaacccag gaggtggagg agaaacttgt gcagaaactg gaatcaatat     2400
tttcttcaca aagattaata aattggctgc tgtaagaatc aatggaatgg tggaaagact     2460
acaactttca cagcaaataa gggagagtgt gtattgtttc ttccaacatg tacttgctca     2520
gcggacttct cttttattca gtcgacacat tgaccagatc attctctgtt gcttctacgg     2580
agtggccaag atatcccaaa tgagcctgac tttcagggaa atcatataca actaccggaa     2640
gcaaccacag tgtaaaccat tagtttttccg cagcgtttat gtggatgcgt tacaatgtcg     2700
ccgtcaaggg agaatagggc cagatcatgt tgacatcatc acattctaca atgaaatatt     2760
tattcctgcc gtaaagccgc tgctggtgga gctaggtcct gtaagaaacg accgggctgt     2820
ggaagccaat aataagcctg aaggtcaatg tcccggatcg ccaaaggtgt ctgtgtttcc     2880
aagtgttcca gacatgtccc ctaaaaaagt atctgcagtg cacaatgttt atgtttctcc     2940
tcttcgggga tcaagatgg atgctcttat ttcacacagt acaaagagtt actatgcttg     3000
tgttggagag agtacacatg cttaccagag cccttcaaag gacctatctg ccatcaacaa     3060
ccgcttgaac aacagcagca gcaaccgcaa gaggacgcta aactttgacg cagaagcagg     3120
gatggtcagc gattccatgg tagcaaatag ccttaacctc caaaaccaaa atcaaaacca     3180
```

```
aaatggaagc gatgcatcgt cctcaggtgg tgccgcaccc cttaaaaccg agccaacaga    3240
ttcatagata tctctctcta cttgctacac caacttctct tcagttatag catctgtaaa    3300
tccttatgtt gcagagtttg cttttatgtt tagctttcta gtttatagtg atcacctcag    3360
gctatgagcg gatggatccc tttattgttt cttttttctt tttttatctt agttaagtca    3420
gtcttaataa gcattaataa atgtcttttt cttgttcaaa aaaaaaaaaa aaaa           3474
```

<210> SEQ ID NO 2  
<211> LENGTH: 1013  
<212> TYPE: PRT  
<213> ORGANISM: Arabidopsis Thaliana

<400> SEQUENCE: 2

```
Met Glu Glu Val Gln Pro Pro Val Thr Pro Pro Ile Glu Pro Asn Gly
1               5                   10                  15

Lys Arg Ser Glu Ala Ser Leu Leu Asp Ile Cys Glu Lys Val Leu Ser
            20                  25                  30

Leu Asp Gly Ser Thr Cys Asp Glu Ala Leu Lys Leu Phe Thr Glu Thr
        35                  40                  45

Lys Arg Ile Leu Ser Ala Ser Met Ser Asn Ile Gly Ser Gly Thr Arg
    50                  55                  60

Glu Glu Val Glu Arg Phe Trp Phe Ala Phe Ile Leu Tyr Ser Val Lys
65                  70                  75                  80

Arg Leu Ser Val Arg Lys Glu Ala Asp Gly Leu Ser Val Ser Gly Asp
                85                  90                  95

Asn Glu Phe Asn Leu Cys Gln Ile Leu Arg Ala Leu Lys Leu Asn Ile
            100                 105                 110

Val Asp Phe Phe Lys Glu Leu Pro Gln Phe Val Val Lys Ala Gly Ser
        115                 120                 125

Val Leu Gly Glu Leu Tyr Gly Ala Asp Trp Glu Asn Arg Leu Gln Ala
    130                 135                 140

Lys Glu Val Gln Ala Asn Phe Val His Leu Ser Leu Leu Ser Lys Tyr
145                 150                 155                 160

Tyr Lys Arg Gly Phe Arg Glu Phe Phe Leu Thr Tyr Asp Ala Asn Ala
                165                 170                 175

Glu Lys Asn Ser Ala Asn Ser Ser Thr Tyr Leu Leu Asp Ser Tyr Arg
            180                 185                 190

Phe Gly Trp Leu Leu Phe Leu Ala Leu Arg Asn His Ala Phe Ser Arg
        195                 200                 205

Phe Lys Asp Leu Val Thr Cys Ser Asn Gly Val Val Ser Ile Leu Ala
    210                 215                 220

Ile Leu Ile Ile His Val Pro Cys Arg Phe Arg Asn Phe Ser Ile Gln
225                 230                 235                 240

Asp Ser Ser Arg Phe Val Lys Lys Gly Asp Lys Gly Val Asp Leu Val
                245                 250                 255

Ala Ser Leu Cys Lys Ile Tyr Asp Ala Ser Glu Asp Glu Leu Arg Ile
            260                 265                 270

Val Ile Asp Lys Ala Asn Asn Leu Val Glu Thr Ile Leu Lys Lys Lys
        275                 280                 285

Pro Ser Pro Ala Ser Glu Cys Gln Thr Asp Lys Leu Asp Asn Ile Asp
    290                 295                 300

Pro Asp Gly Leu Thr Tyr Phe Glu Asp Leu Leu Glu Glu Thr Ser Ile
305                 310                 315                 320
```

-continued

```
Ser Thr Ser Leu Ile Thr Leu Glu Lys Asp Tyr Tyr Asp Gly Lys Gly
            325                 330                 335

Glu Leu Asp Glu Arg Val Phe Ile Asn Glu Asp Ser Leu Leu Gly
        340                 345                 350

Ser Gly Ser Leu Ser Ala Gly Ala Val Asn Ile Thr Gly Val Lys Arg
            355                 360                 365

Lys Ile Asp Ala Leu Ser Ser Pro Ala Arg Thr Phe Ile Ser Pro Leu
370                 375                 380

Ser Pro His Lys Ser Pro Ala Ala Lys Thr Asn Gly Ile Ser Gly Ala
385                 390                 395                 400

Thr Lys Leu Ala Ala Thr Pro Val Ser Thr Ala Met Thr Thr Ala Lys
                405                 410                 415

Trp Leu Arg Thr Val Ile Ser Pro Leu Leu Pro Lys Pro Ser Pro Gly
            420                 425                 430

Leu Glu His Phe Leu Lys Ser Cys Asp Arg Asp Ile Thr Asn Asp Val
        435                 440                 445

Thr Arg Arg Ala His Ile Ile Leu Glu Ala Ile Phe Pro Asn Ser Ser
    450                 455                 460

Leu Gly Ala Gln Cys Gly Gly Ser Leu Gln Ala Val Asp Leu Met
465                 470                 475                 480

Asp Asp Ile Trp Ala Glu Gln Arg Arg Leu Glu Ala Cys Lys Leu Tyr
                485                 490                 495

Tyr Arg Val Leu Glu Ala Met Cys Lys Ala Glu Ala Gln Ile Leu His
            500                 505                 510

Ala Asn Asn Leu Asn Ser Leu Leu Thr Asn Glu Arg Phe His Arg Cys
        515                 520                 525

Met Leu Ala Cys Ser Ala Glu Leu Val Leu Ala Thr His Lys Thr Ile
    530                 535                 540

Thr Met Leu Phe Pro Ala Val Leu Glu Arg Thr Gly Ile Thr Ala Phe
545                 550                 555                 560

Asp Leu Ser Lys Val Ile Glu Ser Phe Ile Arg His Glu Asp Ser Leu
                565                 570                 575

Pro Arg Glu Leu Arg Arg His Leu Asn Ser Leu Glu Glu Arg Leu Leu
            580                 585                 590

Glu Ser Met Val Trp Glu Lys Gly Ser Ser Met Tyr Asn Ser Leu Ile
        595                 600                 605

Val Ala Arg Pro Ser Leu Ala Leu Glu Ile Asn Gln Leu Gly Leu Leu
    610                 615                 620

Ala Glu Pro Met Pro Ser Leu Asp Ala Ile Ala Ala Leu Ile Asn Phe
625                 630                 635                 640

Ser Asp Gly Ala Asn His Ala Ser Ser Val Gln Lys His Glu Thr Cys
                645                 650                 655

Pro Gly Gln Asn Gly Gly Ile Arg Ser Pro Lys Arg Leu Cys Thr Asp
            660                 665                 670

Tyr Arg Ser Ile Leu Val Glu Arg Asn Ser Phe Thr Ser Pro Val Lys
        675                 680                 685

Asp Arg Leu Leu Ala Leu Gly Asn Val Lys Ser Lys Met Leu Pro Pro
    690                 695                 700

Pro Leu Gln Ser Ala Phe Ala Ser Pro Thr Arg Pro Asn Pro Gly Gly
705                 710                 715                 720

Gly Gly Glu Thr Cys Ala Glu Thr Gly Ile Asn Ile Phe Phe Thr Lys
                725                 730                 735

Ile Asn Lys Leu Ala Ala Val Arg Ile Asn Gly Met Val Glu Arg Leu
```

-continued

```
        740                 745                 750
Gln Leu Ser Gln Gln Ile Arg Glu Ser Val Tyr Cys Phe Phe Gln His
            755                 760                 765
Val Leu Ala Gln Arg Thr Ser Leu Leu Phe Ser Arg His Ile Asp Gln
    770                 775                 780
Ile Ile Leu Cys Cys Phe Tyr Gly Val Ala Lys Ile Ser Gln Met Ser
785                 790                 795                 800
Leu Thr Phe Arg Glu Ile Ile Tyr Asn Tyr Arg Lys Gln Pro Gln Cys
                805                 810                 815
Lys Pro Leu Val Phe Arg Ser Val Tyr Val Asp Ala Leu Gln Cys Arg
            820                 825                 830
Arg Gln Gly Arg Ile Gly Pro Asp His Val Asp Ile Ile Thr Phe Tyr
        835                 840                 845
Asn Glu Ile Phe Ile Pro Ala Val Lys Pro Leu Leu Val Glu Leu Gly
    850                 855                 860
Pro Val Arg Asn Asp Arg Ala Val Glu Ala Asn Lys Pro Glu Gly
865                 870                 875                 880
Gln Cys Pro Gly Ser Pro Lys Val Ser Val Phe Pro Ser Val Pro Asp
                885                 890                 895
Met Ser Pro Lys Lys Val Ser Ala Val His Asn Val Tyr Val Ser Pro
            900                 905                 910
Leu Arg Gly Ser Lys Met Asp Ala Leu Ile Ser His Ser Thr Lys Ser
        915                 920                 925
Tyr Tyr Ala Cys Val Gly Glu Ser Thr His Ala Tyr Gln Ser Pro Ser
    930                 935                 940
Lys Asp Leu Ser Ala Ile Asn Asn Arg Leu Asn Asn Ser Ser Ser Asn
945                 950                 955                 960
Arg Lys Arg Thr Leu Asn Phe Asp Ala Glu Ala Gly Met Val Ser Asp
                965                 970                 975
Ser Met Val Ala Asn Ser Leu Asn Leu Gln Asn Gln Asn Gln Asn Gln
            980                 985                 990
Asn Gly Ser Asp Ala Ser Ser  Gly Gly Ala Ala Pro  Leu Lys Thr
        995                 1000                1005
Glu Pro  Thr Asp Ser
    1010
```

<210> SEQ ID NO 3
<211> LENGTH: 4367
<212> TYPE: DNA
<213> ORGANISM: Zea mays

<400> SEQUENCE: 3

```
tcatctcccg ttcaccccgc gggcgcaggg cgcgctctct cctcgtggcg atcgccgacc    60
gtagcggccg ctgcccgggt tttcgtcggc cgcttcgcca tgtcttcgct ggacccttcg   120
ccagcgacga gcacccaaca gaagcaattg agagtttggt aaatctact gacgcaggga    180
agcaggttct accgcaaagc atataatgaa ctgttctcag gtgtaactac tgagcaggat   240
ccggattcat cgactaatat tcctgagtat atgctttttg ggtggcatct cttcttaatg   300
ctccatttga gatcaccaga attgttcaag gacctggtgt cctgcatcca tggattagtt   360
gctgtgttgg ccatactttt gattcacgtg ccagctaaat ttaggagctt cacgattgaa   420
ggctcttctc acttaatcaa acaaactgag aaaggcgtgg atcttattgc ttcattatgt   480
cataactatc ataccctctga agaacgtttg aaagaaatgt tgcacaagtc tcacaatgca   540
```

-continued

```
atagaagaca ttttccatat gaaagcacta agtgcttcag agtgcaaacc agaaaatttg    600
gataagatag acacagatga cctgatgtat ttcaaaggtc tgattgatat ggaatgtttc    660
cagtcaaatt tggaaaaaat ggagaaacta tgtaattcta atagctgtaa agggagctt    720 gattttaaat caattttgat caataatgat tatattccct atgatgagaa ctcgacgggg    780
gattccacca atttaggaca ttcaaagtgt gcctttgaaa cattggcatc tcccacaaag    840
acaataaaga acatgctgac tgttcctagt tctcctttgt caccagccac cggtggttca    900
gtcaagattg tgcaaatgac accagtaact tctgccatga cgacagctaa gtggcttcgt    960
gaggtgatat cttcattgcc agataagcct tcatctaagc ttcagcagtt tctgtcatca   1020
tgcgataggg atttgacaaa tgctgtcaca gaaagggtca gcatagtttt ggaagcaatt   1080
tttccaacca aatcttctgc caatcggggt gtatcgttag gtctcaattg tgcaaatgcc   1140
tttgacattc cgtgggcaga agccagaaaa gtggaggctt ccaagttgta ctatagggta   1200
ttagaggcaa tctgcagagc ggagttacaa acagcaatg taaataatct aactccattg    1260
ctgtcaaatg agcgtttcca ccgatgtttg attgcatgtt cagcggactt agtattggcg   1320
acacataaga cagtcatcat gatgtttcct gctgttcttg agagtaccgg tctaactgca   1380
tttgatttga gcaaaataat tgagaacttt gtgagacatg aagagaccct cccaagagaa   1440
ttgaaaaggc acctaaattc cttagaagaa cagcttttgg aaagcatggc atgggagaaa   1500
ggttcatcat tgtataactc actgattgtt gccaggccat ctgttgcttc agaaataaac   1560
cgccttggtc ttttggctga accaatgcca tctcttgatg acttagtgtc aaggcagaat   1620
gttcgtatcg agggcttgcc tgctacacca tctaaaaaac gtgctgctgg tccagatgac   1680
aacgctgatc ctcgatcacc aaagagatcg tgcaatgaat ctaggaacac agtagtagag   1740
cgcaatttgc agacacctcc acccaagcaa agccacatgg tgtcaactag tttgaaagca   1800
aaatgccatc cactccagtc cacatttgca agtccaactg tctgtaatcc tgttggtggg   1860
aatgaaaaat gtgctgacgt gacaattcat atattctttt ccaagattct gaagttggct   1920
gctattagaa taagaaactt gtgcgaaagg gttcaatgtg tggaacagac agagcgtgtc   1980
tataatgtct tcaagcagat tcttgagcaa cagacaacat tatttttaa tagacacatc   2040 gatcaactta tcctttgctg tctttatggt gttgcaaagg tttgtcaatt agaactcaca   2100
ttcagggaga tactcaacaa ttacaaaaga gaagcacaat gcaagccaga gttttttca    2160 agtatctata ttgggagtac gaaccgtaat ggggtattag tatcgcgcca tgttggtatc   2220
attacttttt acaatgaggt atttgttcca gcagcgaagc ctttcctggt gtcactaata   2280
tcatctggta ctcatccaga agacaagaag aatgctagtg gccaaattcc tggatcaccc   2340
aagccatctc ctttcccaaa tttaccagat atgtccccga agaaagtttc agcatctcat   2400
aatgtatatg tgtctccttt gcggcaaacc aagttggatc tactgctgtc accaagttcc   2460
aggagttttt atgcatgcat tggtgaaggc acccatgctt atcagagccc atctaaggat   2520
ttggctgcta taaatagccg cctaaattat aatggcagga agtaaacag tcgattaaat    2580 ttcgacatgg tgagtgactc agtggtagcc ggcagtctgg gccagataaa tggtggttct   2640
acctcggatc ctgcagctgc atttagcccc ctttcaaaga agagagagac agatacttga   2700
tcaattataa atggtggcct ctctcgtata tagctcacag atccgtgctc cgtagcagtc   2760
tattcttctg aataagtgga ttaactggag cgatttaact gtacatgtat gtgttagtga   2820
gaagcagcag ttttttaggca gcaaactgtt tcaagttagc ttttgagcta tcaccatttc   2880
tctgctgatt gaacatatcc gctgtgtaga gtgctaatga atctttagtt ttcattgggc   2940
```

-continued

```
tgacataaca aatctttatc ctagttggct ggttgttggg aggcattcat cagggttata    3000
tttggttgtc aaaaagtact gtacttaatt cacatctttc acatttttca ctagcaatag    3060
cagccccaaa ttgctttcct gactaggaac atattcttta caggtataag catgccaact    3120
ctaaactata tgaatccttt ttatattctc attttttaagt acttctctgt ttctgctact   3180
tttgtactgt atatttccag cttctccatc agactgatga tcccatattc agtgtgctgc    3240
aagtgatttg acatatgtgg cttatccttc aggtatgtct catgttgtga cttcattgct    3300
gattgctttt gtaatggtac tgttgagttc atttctggtt acaatcagcc tttactgctt    3360
tatattgttc tactaatttt ggcttgcaca gccaggacga ttggttttct gcatcaatca    3420
atctttttta ggacaagata ttttttgtatg ctacacttcc caaattgcaa ttaatccaga   3480
agtctacctt gttttattct attagttctc agcaacagtg aatgaatatg aatcagtcat    3540
gctgatagat gttcatctgg ttattccaaa caatctgaca tcgcatctct ttctgcaagt    3600
gagatgaaga aaacctgaaa tgctatcacc atttaaaaca ttggcttctg aagttcaggt    3660
gattagcagg agacgttctg acattgccat tgacatgtac ggtagtgatg caggagacg     3720 ttcttaaaca gcagctgctc cttcagcttg taatgtctga ttgtattgac caagagcatc    3780
caccttgcct tatggtacta actgaatgag ctggtgacgc tgactcatct gcataatggc    3840
agatgcttaa ccatctttag gagctcatgt catgattcca gctgcaccgt gtgcaaatgt    3900
gaaggccctg caagggcttt ccaggccgca ccaatcctgc ttgcttcttg aagatacata    3960
tggtgccacc taaataaaag ctgtttctgg ttatgtctgt ccttgacatg tcaacagatt    4020
agtgttgggt tgcagtcgtg tggtgtttaa gtcttggaga aggcgagaag tcattgctgc    4080
cagcattgtg tcgtcaggca cagaagtact caaaagtgag agctactttg ttgcgagcaa    4140
acggagggcg ataggttg atagccaatt tcagttctct atatacaagc agcggatttt     4200
gtttagagtt agcttttgag atgcatcatt tctttcacat ctgattctgt gtgttgtaac    4260
tcggagtcgc gtagaagtta gaatgctaac tgacccttaa ttttcaccga ataatttgct    4320 agcgttttc agtatgaaaa aaaaaaaaaa aaaaaaaaa aaaaaaa                    4367
```

<210> SEQ ID NO 4
<211> LENGTH: 866
<212> TYPE: PRT
<213> ORGANISM: Zea Mays

<400> SEQUENCE: 4

```
Met Ser Ser Leu Asp Pro Ser Pro Ala Thr Ser Gln Gln Lys Gln
1               5                   10                  15

Leu Glu Ser Leu Val Asn Leu Leu Thr Gln Gly Ser Arg Phe Tyr Arg
            20                  25                  30

Lys Ala Tyr Asn Glu Leu Phe Ser Gly Val Thr Thr Glu Gln Asp Pro
        35                  40                  45

Asp Ser Ser Thr Asn Ile Pro Glu Tyr Met Leu Phe Gly Trp His Leu
    50                  55                  60

Phe Leu Met Leu His Leu Arg Ser Pro Glu Leu Phe Lys Asp Leu Val
65                  70                  75                  80

Ser Cys Ile His Gly Leu Val Ala Val Leu Ala Ile Leu Leu Ile His
                85                  90                  95

Val Pro Ala Lys Phe Arg Ser Phe Thr Ile Glu Gly Ser Ser His Leu
            100                 105                 110

Ile Lys Gln Thr Glu Lys Gly Val Asp Leu Ile Ala Ser Leu Cys His
```

```
            115                 120                 125
Asn Tyr His Thr Ser Glu Glu Arg Leu Lys Glu Met Leu His Lys Ser
    130                 135                 140
His Asn Ala Ile Glu Asp Ile Phe His Met Lys Ala Leu Ser Ala Ser
145                 150                 155                 160
Glu Cys Lys Pro Glu Asn Leu Asp Lys Ile Asp Thr Asp Leu Met
                165                 170                 175
Tyr Phe Lys Gly Leu Ile Asp Met Glu Cys Phe Gln Ser Asn Leu Glu
                180                 185                 190
Lys Met Glu Lys Leu Cys Asn Ser Asn Ser Cys Lys Gly Glu Leu Asp
                195                 200                 205
Phe Lys Ser Ile Leu Ile Asn Asn Asp Tyr Ile Pro Tyr Asp Glu Asn
    210                 215                 220
Ser Thr Gly Asp Ser Thr Asn Leu Gly His Ser Lys Cys Ala Phe Glu
225                 230                 235                 240
Thr Leu Ala Ser Pro Thr Lys Thr Ile Lys Asn Met Leu Thr Val Pro
                245                 250                 255
Ser Ser Pro Leu Ser Pro Ala Thr Gly Gly Ser Val Lys Ile Val Gln
                260                 265                 270
Met Thr Pro Val Thr Ser Ala Met Thr Thr Ala Lys Trp Leu Arg Glu
                275                 280                 285
Val Ile Ser Ser Leu Pro Asp Lys Pro Ser Ser Lys Leu Gln Gln Phe
    290                 295                 300
Leu Ser Ser Cys Asp Arg Asp Leu Thr Asn Ala Val Thr Glu Arg Val
305                 310                 315                 320
Ser Ile Val Leu Glu Ala Ile Phe Pro Thr Lys Ser Ser Ala Asn Arg
                325                 330                 335
Gly Val Ser Leu Gly Leu Asn Cys Ala Asn Ala Phe Asp Ile Pro Trp
                340                 345                 350
Ala Glu Ala Arg Lys Val Glu Ala Ser Lys Leu Tyr Tyr Arg Val Leu
                355                 360                 365
Glu Ala Ile Cys Arg Ala Glu Leu Gln Asn Ser Asn Val Asn Asn Leu
    370                 375                 380
Thr Pro Leu Leu Ser Asn Glu Arg Phe His Arg Cys Leu Ile Ala Cys
385                 390                 395                 400
Ser Ala Asp Leu Val Leu Ala Thr His Lys Thr Val Ile Met Met Phe
                405                 410                 415
Pro Ala Val Leu Glu Ser Thr Gly Leu Thr Ala Phe Asp Leu Ser Lys
                420                 425                 430
Ile Ile Glu Asn Phe Val Arg His Glu Glu Thr Leu Pro Arg Glu Leu
                435                 440                 445
Lys Arg His Leu Asn Ser Leu Glu Glu Gln Leu Leu Glu Ser Met Ala
    450                 455                 460
Trp Glu Lys Gly Ser Ser Leu Tyr Asn Ser Leu Ile Val Ala Arg Pro
465                 470                 475                 480
Ser Val Ala Ser Glu Ile Asn Arg Leu Gly Leu Leu Ala Glu Pro Met
                485                 490                 495
Pro Ser Leu Asp Asp Leu Val Ser Arg Gln Asn Val Arg Ile Glu Gly
                500                 505                 510
Leu Pro Ala Thr Pro Ser Lys Lys Arg Ala Ala Gly Pro Asp Asp Asn
                515                 520                 525
Ala Asp Pro Arg Ser Pro Lys Arg Ser Cys Asn Glu Ser Arg Asn Thr
    530                 535                 540
```

```
Val Val Glu Arg Asn Leu Gln Thr Pro Pro Lys Gln Ser His Met
545                 550                 555                 560

Val Ser Thr Ser Leu Lys Ala Lys Cys His Pro Leu Gln Ser Thr Phe
                565                 570                 575

Ala Ser Pro Thr Val Cys Asn Pro Val Gly Gly Asn Glu Lys Cys Ala
                580                 585                 590

Asp Val Thr Ile His Ile Phe Phe Ser Lys Ile Leu Lys Leu Ala Ala
            595                 600                 605

Ile Arg Ile Arg Asn Leu Cys Glu Arg Val Gln Cys Val Glu Gln Thr
    610                 615                 620

Glu Arg Val Tyr Asn Val Phe Lys Gln Ile Leu Glu Gln Gln Thr Thr
625                 630                 635                 640

Leu Phe Phe Asn Arg His Ile Asp Gln Leu Ile Leu Cys Cys Leu Tyr
                645                 650                 655

Gly Val Ala Lys Val Cys Gln Leu Glu Leu Thr Phe Arg Glu Ile Leu
                660                 665                 670

Asn Asn Tyr Lys Arg Glu Ala Gln Cys Lys Pro Glu Val Phe Ser Ser
            675                 680                 685

Ile Tyr Ile Gly Ser Thr Asn Arg Asn Gly Val Leu Val Ser Arg His
    690                 695                 700

Val Gly Ile Ile Thr Phe Tyr Asn Glu Val Phe Val Pro Ala Ala Lys
705                 710                 715                 720

Pro Phe Leu Val Ser Leu Ile Ser Ser Gly Thr His Pro Glu Asp Lys
                725                 730                 735

Lys Asn Ala Ser Gly Gln Ile Pro Gly Ser Pro Lys Pro Ser Pro Phe
                740                 745                 750

Pro Asn Leu Pro Asp Met Ser Pro Lys Lys Val Ser Ala Ser His Asn
            755                 760                 765

Val Tyr Val Ser Pro Leu Arg Gln Thr Lys Leu Asp Leu Leu Leu Ser
    770                 775                 780

Pro Ser Arg Ser Phe Tyr Ala Cys Ile Gly Glu Gly Thr His Ala
785                 790                 795                 800

Tyr Gln Ser Pro Ser Lys Asp Leu Ala Ala Ile Asn Ser Arg Leu Asn
                805                 810                 815

Tyr Asn Gly Arg Lys Val Asn Ser Arg Leu Asn Phe Asp Met Val Ser
            820                 825                 830

Asp Ser Val Val Ala Gly Ser Leu Gly Gln Ile Asn Gly Gly Ser Thr
    835                 840                 845

Ser Asp Pro Ala Ala Ala Phe Ser Pro Leu Ser Lys Lys Arg Glu Thr
850                 855                 860

Asp Thr
865

<210> SEQ ID NO 5
<211> LENGTH: 2945
<212> TYPE: DNA
<213> ORGANISM: Zea mays

<400> SEQUENCE: 5
gagaattgaa aagacaccta aattccttag aagaacaaat tttggaaagc atggcatggg      60
agaaaggttc atcattgtat aactcactga ttgttgccag gccatctgtt gcttcagaaa     120
ttaatcgctt tggtcttctg gctgaatcaa tgccatctct tgatgactta gtggcaaggc     180
agaatattca tattgagggc ttgcctgcta caccatctaa aaaacgtgct gctggtcgag     240
```

-continued

| | |
|---|---|
| acgacaatgc tgatcctcga tcaccaaaga gaccatgcaa tgaatctagg agcacagtag | 300 |
| tagaacacaa tttgcagaca cctccaccca agcaatgcca catggtgttg actagtttga | 360 |
| aagcaaaatg ccatccactc cagtccacat ttgcaagtcc aactgtcagt aatcctgttg | 420 |
| gtgggaacga aaatgtgct gacgtgacaa ttcagatatt cttttccaaa attctgaagt | 480 |
| tagctgctat tagaataaga aacttgtgtg aaaggattca atatatggaa cagacagagc | 540 |
| gtgtctataa tgtcttcaag cagattcttg atcaacagac aacattattt tttaatagac | 600 |
| acatgcatca acttattctt tgctgtcttt atggtgttgc aaaggtttgc caattagaac | 660 |
| tctcattcag ggagatactc aacaattaca aaaagaagc acaatgcaaa ccagaagttt | 720 |
| ttttaagcat ctatattgga agtaggaatc ataatgggt attaatatca cgccatgttg | 780 |
| atatcattac ttttacaat gaggtctttg ttccagcagc caagcctttc ctggtgtcat | 840 |
| taatatcatc tggtactcgt ccagaagaca agaagaatgc tagtggccaa gttcctggat | 900 |
| caccgaagct atctcctttc ccaaatttac cagatatgtc cccaaagaaa gtttcagctt | 960 |
| ctcataatgt atatgtgtct cctttgcggc aaaccaagat ggatttactg ctgtcaccaa | 1020 |
| gttccaggag ttttatgca tgcattggtg aaggcaccca tgcttatcag agcccatcta | 1080 |
| aagatttggc tgctataaat agccgcctaa attataatgg tcggagagta aacagtcgat | 1140 |
| taaactttga catggtgagc gactcagtgg tagctggtag tctaggccag ccaaatggtg | 1200 |
| gttctacttc cttggatcct gcagctgcat ttagccccct ttcaaagaga aagccagata | 1260 |
| cttgatcaaa tataaatggc gatctctctc gtatatagct cacagctcca tagcagtcta | 1320 |
| ttcttctgaa taagtgggtt gactggagtg atttaactgt acatgtatgt gttagtgaga | 1380 |
| accagcagtt tataggcagc aaactgtttt aaattagctt tgaggtttta tcaccatttc | 1440 |
| cctgctgatt gaacatattt tagattgtaa catctgcttt gtagaatgct aatgaatctt | 1500 |
| tagttttcag tgggttgaca ttaaaaatcc ttatcctagt tggctggttg ttgggagaca | 1560 |
| ttcatcaagg ttatatttgg tcgtcaaata gtactgtact tgattcatat ctttcatatt | 1620 |
| tttcactagc gttggcaacc gtaaattgct ttcctgacta ggaacatatt cttcacaagt | 1680 |
| atggcaactc taaactattt gaccttttat attctcattt ttaagtactt tctctatttc | 1740 |
| tgctactttt gtactgtgta tttccagctt ctccaccaga ctgattgtta gagtgtatgc | 1800 |
| tcctatatta tccatgtatg tgtaaatggg ctgctagccc attagggtta ggttcccctg | 1860 |
| ggtctatata tgtaaccacc ctctatgcaa tagaagttga atatcagttt ctatcactaa | 1920 |
| tgattccata ttcagtgggc tgcaagtgat ttgacatacg tgccttatcc ttcaggtatg | 1980 |
| tctcatgttg actttgcttt tgtaatggta ctgttggctt cattgctgga atgctggtta | 2040 |
| taatcaacct ttactgctct atattgttct ttttttggtt tgcacaacca gggtggttgg | 2100 |
| ttttctgaat caatcaatcc atttcctcgg acgacaagat aattttttgta tgttacactt | 2160 |
| cccaaaattg caattaattc agaagtctgc ctactttcat tcagttagtt ctcagcaaca | 2220 |
| ctgaaaggat atgaatcagt caacccgata gatgtttatc tggttattcc aaacaatctg | 2280 |
| acatcacatc tgtttctgca ggcgagataa ggaaaatctg aaatgctatc accatttaaa | 2340 |
| acattggctc ctggaagttc aggtaggtgt tgctgtagaa tgagatggtt aggaatcttt | 2400 |
| acaagctcag gctatatgat ttcagcagca ctgtaacctg gggtgcaaat gttaaggccc | 2460 |
| tgcaagcact ttccaggcca caccaattct gcttggttct tgaagataca ttcttcctat | 2520 |
| gtgcccccta tataaaagcc atttctggtt gttatgttta tccttgacat gtcaacagat | 2580 |

-continued

```
tagtgttggg ttgcagtcat gcggtccta agtctcggag aaggcgagaa gtcattgctg    2640
ctagcattgt gatcgtcggc cacgaaagta atcaaaaagt gagagctact tgttcctagc    2700
aaatggagaa gggcgatata taggtttatg atcaaattca gtgtatgcaa gcagcatatt    2760
ttgtttagag ttagcttttg aggttcatca tttcatttca cagctgattc tctatgttgt    2820
aactccttag tcgtgtagaa attagaatgc tatctgctta attttagtg aataatttgc    2880 tagtatattt ttgaatgtaa ttgcagtagc tctgcctctt cattaaggaa aaaaaaaaa    2940 aaaaa                                                                 2945
```

<210> SEQ ID NO 6
<211> LENGTH: 420
<212> TYPE: PRT
<213> ORGANISM: Zea mays

<400> SEQUENCE: 6

```
Glu Leu Lys Arg His Leu Asn Ser Leu Glu Glu Gln Ile Leu Glu Ser
 1               5                  10                  15

Met Ala Trp Glu Lys Gly Ser Ser Leu Tyr Asn Ser Leu Ile Val Ala
            20                  25                  30

Arg Pro Ser Val Ala Ser Glu Ile Asn Arg Phe Gly Leu Leu Ala Glu
        35                  40                  45

Ser Met Pro Ser Leu Asp Asp Leu Val Ala Arg Gln Asn Ile His Ile
    50                  55                  60

Glu Gly Leu Pro Ala Thr Pro Ser Lys Lys Arg Ala Ala Gly Arg Asp
65                  70                  75                  80

Asp Asn Ala Asp Pro Arg Ser Pro Lys Arg Pro Cys Asn Glu Ser Arg
                85                  90                  95

Ser Thr Val Val Glu His Asn Leu Gln Thr Pro Pro Lys Gln Cys
            100                 105                 110

His Met Val Leu Thr Ser Leu Lys Ala Lys Cys His Pro Leu Gln Ser
        115                 120                 125

Thr Phe Ala Ser Pro Thr Val Ser Asn Pro Val Gly Gly Asn Glu Lys
    130                 135                 140

Cys Ala Asp Val Thr Ile Gln Ile Phe Phe Ser Lys Ile Leu Lys Leu
145                 150                 155                 160

Ala Ala Ile Arg Ile Arg Asn Leu Cys Glu Arg Ile Gln Tyr Met Glu
                165                 170                 175

Gln Thr Glu Arg Val Tyr Asn Val Phe Lys Gln Ile Leu Asp Gln Gln
            180                 185                 190

Thr Thr Leu Phe Phe Asn Arg His Met His Gln Leu Ile Leu Cys Cys
        195                 200                 205

Leu Tyr Gly Val Ala Lys Val Cys Gln Leu Glu Leu Ser Phe Arg Glu
    210                 215                 220

Ile Leu Asn Asn Tyr Lys Lys Glu Ala Gln Cys Lys Pro Glu Val Phe
225                 230                 235                 240

Leu Ser Ile Tyr Ile Gly Ser Arg Asn His Asn Gly Val Leu Ile Ser
                245                 250                 255

Arg His Val Asp Ile Ile Thr Phe Tyr Asn Glu Val Phe Val Pro Ala
            260                 265                 270

Ala Lys Pro Phe Leu Val Ser Leu Ile Ser Ser Gly Thr Arg Pro Glu
        275                 280                 285

Asp Lys Lys Asn Ala Ser Gly Gln Val Pro Gly Ser Pro Lys Leu Ser
    290                 295                 300
```

| | | | | | | | | | | | | | | |
|---|---|---|---|---|---|---|---|---|---|---|---|---|---|---|
| Pro | Phe | Pro | Asn | Leu | Pro | Asp | Met | Ser | Pro | Lys | Lys | Val | Ser | Ala | Ser |
| 305 | | | | 310 | | | | 315 | | | | | 320 | | |

His Asn Val Tyr Val Ser Pro Leu Arg Gln Thr Lys Met Asp Leu Leu
                 325                     330               335

Leu Ser Pro Ser Ser Arg Ser Phe Tyr Ala Cys Ile Gly Glu Gly Thr
           340                   345                  350

His Ala Tyr Gln Ser Pro Ser Lys Asp Leu Ala Ala Ile Asn Ser Arg
       355                  360              365

Leu Asn Tyr Asn Gly Arg Arg Val Asn Ser Arg Leu Asn Phe Asp Met
     370                  375              380

Val Ser Asp Ser Val Val Ala Gly Ser Leu Gly Gln Pro Asn Gly Gly
385                   390                    395              400

Ser Thr Ser Leu Asp Pro Ala Ala Ala Phe Ser Pro Leu Ser Lys Arg
           405                  410              415

Lys Pro Asp Thr
        420

<210> SEQ ID NO 7
<211> LENGTH: 2538
<212> TYPE: DNA
<213> ORGANISM: Zea mays

<400> SEQUENCE: 7

| | | | | |
|---|---|---|---|---|
| cctagttccc | ctttgtcacc | caccaacggt | ggttcagtca | agattgtgca aatgacacca | 60 |
| ataacttctg | ccatgacgac | agctaagtgg | cttcgtgagg | tgatatcttc attgccagag | 120 |
| aagccttcat | ctaagcttca | gcagttgatg | tcatcatgcg | atagagattt gacaaatgcc | 180 |
| gtcacagaaa | gggtcagcat | agttctggaa | gcaattttc | caaccaagtc ttctgctgat | 240 |
| cggggtggct | cattaggcct | caattgtgca | atgcctttg | atactctatg ggcagatgcc | 300 |
| agaaaaatgg | aggcttccaa | gttgtactat | agggtattag | aggcaatctg cagagctgag | 360 |
| ttacaaaaca | gcaatgtaaa | caatctaact | ccattgctgt | caaatgagcg ttttcaccga | 420 |
| tgtttgattg | catgttcagc | ggagctagta | ttggcgacac | ataagacggt catcatgatg | 480 |
| tttcctgctg | ttcttgagag | tactggtcta | acctcatttg | atttgagcaa ataattgag | 540 |
| aactttgtga | acatgaaga | gaccctccca | agagaattga | aaagacacct aaattcctta | 600 |
| gaagaacaaa | ttttggaaag | catggcatgg | gagaaaggtt | catcattgta taactcactg | 660 |
| attgttgcca | ggccatctgt | tgcttcagaa | attaatcgct | ttggtcttct ggctgaatca | 720 |
| atgccatctc | ttgatgactt | agtggcaagg | cagaatattc | atattgaggg cttgcctgct | 780 |
| acaccatcta | aaaaacgtgc | tgctggtcga | gacgacaatg | ctgatcctcg atcaccaaag | 840 |
| agaccatgca | atgaatctag | gagcacagta | gtagaacaca | atttgcagac cctccaccc | 900 |
| aagcaatgcc | acatggtgtt | gactagtttg | aaagcaaaat | gccatccact ccagtccaca | 960 |
| tttgcaagtc | caactgtcag | taatcctgtt | ggtgggaacg | aaaaatgtgc tgacgtgaca | 1020 |
| attcagatat | tcttttccaa | aattctgaag | ttagctgcta | ttagaataag aaacttgtgt | 1080 |
| gaaaggattc | aatatatgga | acagacagag | cgtgtctata | atgtcttcaa gcagattctt | 1140 |
| gatcaacaga | caacattatt | ttttaataga | cacatgcatc | aacttattct tgctgtctt | 1200 |
| tatggtgttg | caaggtttg | ccaattagaa | ctctcattca | gggagatact caacaattac | 1260 |
| aaaaagaag | cacaatgcaa | accagaagtt | tttttaagca | tctatattgg aagtaggaat | 1320 |
| cataatgggg | tattaatatc | acgccatgtt | gatatcatta | cttttacaa tgaggtctt | 1380 |
| gttccagcag | ccaagccttt | cctggtgtca | ttaatatcat | ctggtactcg tccagaagac | 1440 |

```
aagaagaatg ctagtggcca agttcctgga tcaccgaagc tatctccttt cccaaattta    1500
ccagatatgt ccccaaagaa agtttcagct tctcataatg tatatgtgtc tcctttgcgg    1560
caaaccaaga tggatttact gctgtcacca agttccagga gttttatgc atgcattggt     1620 gaaggcaccc atgcttatca gagcccatct aaagatttgg ctgctataaa tagccgccta    1680
aattataatg tcggagagt aaacagtcga ttaaactttg acatggtatg tctcatgttg     1740
actttgcttt tgtaatggta ctgttggctt cattgctgga atgctggtta taatcaacct    1800
ttactgctct atattgttct tttttggtt tgcacaacca gggtggttgg ttttctgaat     1860
caatcaatcc atttcctcgg acacaagata atttttgcga gataaggaaa atctgaaatg    1920
ctatcaccat ttaaaacatt ggctcctgga agttcaggtt aggtgttgct gtagaatgag    1980
atggttacca tctttacaag ctcaggctat atgatttcag cagcactgta acctggggtg    2040
caaatgttaa ggccctgcaa gcactttcca ggccacacca attctgcttg gttcttgaag    2100
atacattctt cctatgtgcc ccctatataa aagccatttc tggttgttat gtttatcctt    2160
gacatgtcaa cagattagtg ttgggttgca gtcatgcggt ccttaagtct cggagaaggc    2220
gagaagtcat tgctgctagc attgtgatcg tcggccacga aagtaatcaa aaagtgagag    2280
ctacttgttc ctagcaaatg gagaagggcg atatataggt ttatgatcaa attcagtgta    2340
tgcaagcagc atattttgtt tagagttagc ttttgaggtt catcatttca tttcacagct    2400
gattctctat gttgtaactc cttagtcgtg tagaaattag aatgctatct gcttaatttt    2460
tagtgaataa tttgctagta tatttttgaa tgtaattgca gtagctctgc ctcttcatta    2520
aaaaaaaaaa aaaaaaaa                                                  2538

<210> SEQ ID NO 8
<211> LENGTH: 584
<212> TYPE: PRT
<213> ORGANISM: Zea mays

<400> SEQUENCE: 8

Pro Ser Ser Pro Leu Ser Pro Thr Asn Gly Gly Ser Val Lys Ile Val
1               5                   10                  15

Gln Met Thr Pro Ile Thr Ser Ala Met Thr Thr Ala Lys Trp Leu Arg
            20                  25                  30

Glu Val Ile Ser Ser Leu Pro Glu Lys Pro Ser Ser Lys Leu Gln Gln
        35                  40                  45

Leu Met Ser Ser Cys Asp Arg Asp Leu Thr Asn Ala Val Thr Glu Arg
    50                  55                  60

Val Ser Ile Val Leu Glu Ala Ile Phe Pro Thr Lys Ser Ser Ala Asp
65                  70                  75                  80

Arg Gly Gly Ser Leu Gly Leu Asn Cys Ala Asn Ala Phe Asp Thr Leu
                85                  90                  95

Trp Ala Asp Ala Arg Lys Met Glu Ala Ser Lys Leu Tyr Tyr Arg Val
            100                 105                 110

Leu Glu Ala Ile Cys Arg Ala Glu Leu Gln Asn Ser Asn Val Asn Asn
        115                 120                 125

Leu Thr Pro Leu Leu Ser Asn Glu Arg Phe His Arg Cys Leu Ile Ala
    130                 135                 140

Cys Ser Ala Glu Leu Val Leu Ala Thr His Lys Thr Val Ile Met Met
145                 150                 155                 160

Phe Pro Ala Val Leu Glu Ser Thr Gly Leu Thr Ser Phe Asp Leu Ser
                165                 170                 175
```

```
Lys Ile Ile Glu Asn Phe Val Arg His Glu Thr Leu Pro Arg Glu
            180                 185                 190
Leu Lys Arg His Leu Asn Ser Leu Glu Glu Gln Ile Leu Glu Ser Met
        195                 200                 205
Ala Trp Glu Lys Gly Ser Ser Leu Tyr Asn Ser Leu Ile Val Ala Arg
        210                 215                 220
Pro Ser Val Ala Ser Glu Ile Asn Arg Phe Gly Leu Leu Ala Glu Ser
225                 230                 235                 240
Met Pro Ser Leu Asp Asp Leu Val Ala Arg Gln Asn Ile His Ile Glu
                245                 250                 255
Gly Leu Pro Ala Thr Pro Ser Lys Lys Arg Ala Ala Gly Arg Asp Asp
                260                 265                 270
Asn Ala Asp Pro Arg Ser Pro Lys Arg Pro Cys Asn Glu Ser Arg Ser
            275                 280                 285
Thr Val Val Glu His Asn Leu Gln Thr Pro Pro Lys Gln Cys His
        290                 295                 300
Met Val Leu Thr Ser Leu Lys Ala Lys Cys His Pro Leu Gln Ser Thr
305                 310                 315                 320
Phe Ala Ser Pro Thr Val Ser Asn Pro Val Gly Gly Asn Glu Lys Cys
                325                 330                 335
Ala Asp Val Thr Ile Gln Ile Phe Phe Ser Lys Ile Leu Lys Leu Ala
                340                 345                 350
Ala Ile Arg Ile Arg Asn Leu Cys Glu Arg Ile Gln Tyr Met Glu Gln
            355                 360                 365
Thr Glu Arg Val Tyr Asn Val Phe Lys Gln Ile Leu Asp Gln Gln Thr
        370                 375                 380
Thr Leu Phe Phe Asn Arg His Met His Gln Leu Ile Leu Cys Cys Leu
385                 390                 395                 400
Tyr Gly Val Ala Lys Val Cys Gln Leu Glu Leu Ser Phe Arg Glu Ile
                405                 410                 415
Leu Asn Asn Tyr Lys Lys Glu Ala Gln Cys Lys Pro Glu Val Phe Leu
            420                 425                 430
Ser Ile Tyr Ile Gly Ser Arg Asn His Asn Gly Val Leu Ile Ser Arg
        435                 440                 445
His Val Asp Ile Ile Thr Phe Tyr Asn Glu Val Phe Val Pro Ala Ala
    450                 455                 460
Lys Pro Phe Leu Val Ser Leu Ile Ser Ser Gly Thr Arg Pro Glu Asp
465                 470                 475                 480
Lys Lys Asn Ala Ser Gly Gln Val Pro Gly Ser Pro Lys Leu Ser Pro
                485                 490                 495
Phe Pro Asn Leu Pro Asp Met Ser Pro Lys Lys Val Ser Ala Ser His
            500                 505                 510
Asn Val Tyr Val Ser Pro Leu Arg Gln Thr Lys Met Asp Leu Leu Leu
        515                 520                 525
Ser Pro Ser Ser Arg Ser Phe Tyr Ala Cys Ile Gly Glu Gly Thr His
530                 535                 540
Ala Tyr Gln Ser Pro Ser Lys Asp Leu Ala Ala Ile Asn Ser Arg Leu
545                 550                 555                 560
Asn Tyr Asn Gly Arg Arg Val Asn Ser Arg Leu Asn Phe Asp Met Val
                565                 570                 575
Cys Leu Met Leu Thr Leu Leu Leu
                580
```

```
<210> SEQ ID NO 9
<211> LENGTH: 6422
<212> TYPE: DNA
<213> ORGANISM: Arabidopsis Thaliana
<220> FEATURE:
<221> NAME/KEY: promoter
<222> LOCATION: (1)..(543)
<223> OTHER INFORMATION:
<220> FEATURE:
<221> NAME/KEY: 5'UTR
<222> LOCATION: (544)..(653)
<223> OTHER INFORMATION:
<220> FEATURE:
<221> NAME/KEY: Intron
<222> LOCATION: (654)..(1093)
<223> OTHER INFORMATION:
<220> FEATURE:
<221> NAME/KEY: 5'UTR
<222> LOCATION: (1094)..(1107)
<223> OTHER INFORMATION:
<220> FEATURE:
<221> NAME/KEY: exon
<222> LOCATION: (1108)..(1189)
<223> OTHER INFORMATION:
<220> FEATURE:
<221> NAME/KEY: Intron
<222> LOCATION: (1190)..(1307)
<223> OTHER INFORMATION:
<220> FEATURE:
<221> NAME/KEY: exon
<222> LOCATION: (1308)..(1410)
<223> OTHER INFORMATION:
<220> FEATURE:
<221> NAME/KEY: Intron
<222> LOCATION: (1411)..(1497)
<223> OTHER INFORMATION:
<220> FEATURE:
<221> NAME/KEY: exon
<222> LOCATION: (1498)..(1641)
<223> OTHER INFORMATION:
<220> FEATURE:
<221> NAME/KEY: Intron
<222> LOCATION: (1642)..(1721)
<223> OTHER INFORMATION:
<220> FEATURE:
<221> NAME/KEY: exon
<222> LOCATION: (1722)..(1817)
<223> OTHER INFORMATION:
<220> FEATURE:
<221> NAME/KEY: Intron
<222> LOCATION: (1818)..(1902)
<223> OTHER INFORMATION:
<220> FEATURE:
<221> NAME/KEY: exon
<222> LOCATION: (1903)..(1951)
<223> OTHER INFORMATION:
<220> FEATURE:
<221> NAME/KEY: Intron
<222> LOCATION: (1952)..(2216)
<223> OTHER INFORMATION:
<220> FEATURE:
<221> NAME/KEY: exon
<222> LOCATION: (2217)..(2409)
<223> OTHER INFORMATION:
<220> FEATURE:
<221> NAME/KEY: Intron
<222> LOCATION: (2410)..(2540)
<223> OTHER INFORMATION:
<220> FEATURE:
<221> NAME/KEY: exon
<222> LOCATION: (2541)..(2606)
<223> OTHER INFORMATION:
<220> FEATURE:
<221> NAME/KEY: Intron
<222> LOCATION: (2607)..(2693)
<223> OTHER INFORMATION:
<220> FEATURE:
<221> NAME/KEY: exon
```

```
<222> LOCATION: (2694)..(2873)
<223> OTHER INFORMATION:
<220> FEATURE:
<221> NAME/KEY: Intron
<222> LOCATION: (2874)..(2973)
<223> OTHER INFORMATION:
<220> FEATURE:
<221> NAME/KEY: exon
<222> LOCATION: (2974)..(4029)
<223> OTHER INFORMATION:
<220> FEATURE:
<221> NAME/KEY: Intron
<222> LOCATION: (4030)..(4124)
<223> OTHER INFORMATION:
<220> FEATURE:
<221> NAME/KEY: exon
<222> LOCATION: (4125)..(4287)
<223> OTHER INFORMATION:
<220> FEATURE:
<221> NAME/KEY: Intron
<222> LOCATION: (4288)..(4385)
<223> OTHER INFORMATION:
<220> FEATURE:
<221> NAME/KEY: exon
<222> LOCATION: (4386)..(4458)
<223> OTHER INFORMATION:
<220> FEATURE:
<221> NAME/KEY: Intron
<222> LOCATION: (4459)..(4579)
<223> OTHER INFORMATION:
<220> FEATURE:
<221> NAME/KEY: exon
<222> LOCATION: (4580)..(4756)
<223> OTHER INFORMATION:
<220> FEATURE:
<221> NAME/KEY: Intron
<222> LOCATION: (4757)..(4869)
<223> OTHER INFORMATION:
<220> FEATURE:
<221> NAME/KEY: exon
<222> LOCATION: (4870)..(4969)
<223> OTHER INFORMATION:
<220> FEATURE:
<221> NAME/KEY: Intron
<222> LOCATION: (4970)..(5051)
<223> OTHER INFORMATION:
<220> FEATURE:
<221> NAME/KEY: exon
<222> LOCATION: (5052)..(5184)
<223> OTHER INFORMATION:
<220> FEATURE:
<221> NAME/KEY: Intron
<222> LOCATION: (5185)..(5276)
<223> OTHER INFORMATION:
<220> FEATURE:
<221> NAME/KEY: exon
<222> LOCATION: (5277)..(5390)
<223> OTHER INFORMATION:
<220> FEATURE:
<221> NAME/KEY: Intron
<222> LOCATION: (5391)..(5497)
<223> OTHER INFORMATION:
<220> FEATURE:
<221> NAME/KEY: exon
<222> LOCATION: (5498)..(5613)
<223> OTHER INFORMATION:
<220> FEATURE:
<221> NAME/KEY: Intron
<222> LOCATION: (5614)..(5695)
<223> OTHER INFORMATION:
<220> FEATURE:
<221> NAME/KEY: exon
<222> LOCATION: (5696)..(5870)
<223> OTHER INFORMATION:
<220> FEATURE:
<221> NAME/KEY: 3'UTR
<222> LOCATION: (5871)..(6081)
<223> OTHER INFORMATION:
<220> FEATURE:
```

-continued

```
<221> NAME/KEY: misc_feature
<222> LOCATION: (6082)..(6421)
<223> OTHER INFORMATION:

<400> SEQUENCE: 9
```

| | |
|---|---|
| gatcctactc acactcgaag atgacgaaga agacttaatc tgaatccatc cgcggatagg | 60 |
| acactcatac ttctgcaacc aaacgttcta caatggcaaa tatgtaattt cccgcgtgac | 120 |
| ctaaactaga aacggcatcg tattaagggt gggcccaatc ataactcaca cgaggctttg | 180 |
| tcgcggtcac gaaaacccag acggcgttaa tggcccactc cgtttgtttc gaccccgccg | 240 |
| tgacggcgaa tctttccctc tcagcgtttc acgcaacagt aagtaagttt tggcggtaaa | 300 |
| attgggtcac agatgggtac gtgtcgattt aatagtggtt gaaagcgcgc gaatataatt | 360 |
| gtatacgtat gtgtatgtat tctccgtgtt gttttcccg cgcgagatat atccttttt | 420 |
| aggtttgcc gcataatcag accccattct agagagagaa gagggaagtc aggtgaagat | 480 |
| agagagagac actgagagga gggaaaattt gtagggtttc cggagatctc tgtgattcct | 540 |
| ctgaatttgt cgaattttt ggaggaggcg ttagaagtcg ggcttcttaa aaatcagatc | 600 |
| ttctgctcag cttaatcgg cgacgtctgg tattgggatc tgtgacacaa aaaggtaaga | 660 |
| tctttctcta ttgcctatcc tttgatttga atcttatcc tctaggtggt ttatctgaaa | 720 |
| ttttctattg atatttcgct attcgattgt aagttggtga gagaattctc caaaaacaaa | 780 |
| aaagagaaaa actttgaatg aatatttaag ataacatctg ggtaaaattt ttccggagtg | 840 |
| gtgggttta gattatgccc caatttctct tcttttttc ccccaaattt tgtctttctg | 900 |
| ccatgttttg ggaaattggg agtttgtttt ctcatgtctg ttagtgtgtt cttccgaatg | 960 |
| ggttgggcat ggttcctatt gaatttcagt gtgattaaat taacaaatct ctttgcttga | 1020 |
| aaagtccctt tttcttcgtc ttcagttagc agtttaattg gaagtaaaat tagcttgatt | 1080 |

| | | |
|---|---|---|
| ttgcatgttt tcagctgcgt tggagac tat gga aga agt tca gcc tcc agt gac | | 1134 |
| Tyr Gly Arg Ser Ser Ala Ser Ser Asp | | |
| 1 5 | | |
| ccc gcc cat tga acc aaa tgg gaa aag aag cga agc ctc tct ctt gga | | 1182 |
| Pro Ala His Thr Lys Trp Glu Lys Lys Arg Ser Leu Ser Leu Gly | | |
| 10 15 20 | | |
| cat atg c gaggtttact cttctctttg ctgatctagt tgcatttgtt tagttgaaga | | 1239 |
| His Met | | |
| 25 | | |
| taccatttga gttctctcgg aaattttgag gactagctct aatccctgta gttgatttct | | 1299 |
| tattgcag aa agt tct gtc tct tga tgg gag cac ttg cga tga agc ttt | | 1348 |
| Gln Ser Ser Val Ser Trp Glu His Leu Arg Ser Phe | | |
| 30 35 | | |
| gaa gtt gtt tac aga aac caa acg aat ttt gtc agc aag cat gtc taa | | 1396 |
| Glu Val Val Tyr Arg Asn Gln Thr Asn Phe Val Ser Lys His Val | | |
| 40 45 50 | | |
| cat tgg aag tgg aa cggtgaaata cattttcct ctaacttctc ttttatcagt | | 1450 |
| His Trp Lys Trp Lys | | |
| 55 | | |
| taactgtggt ttcattatga ctaaatcctt ttttcttctt cttatta g cgg gaa gaa | | 1507 |
| Arg Glu Glu | | |
| 60 | | |
| gta gag agg ttc tgg ttt gcg ttt att ctc tat tca gtg aag agg ctt | | 1555 |
| Val Glu Arg Phe Trp Phe Ala Phe Ile Leu Tyr Ser Val Lys Arg Leu | | |
| 65 70 75 | | |
| agt gtg aga aaa gaa gcg gat ggt ctg tca gtg tct ggt gat aat gag | | 1603 |
| Ser Val Arg Lys Glu Ala Asp Gly Leu Ser Val Ser Gly Asp Asn Glu | | |
| 80 85 90 | | |

-continued

```
ttt aat cta tgt cag ata ctg agg gct ctg aag cta aa  gtaagtagtg    1651
Phe Asn Leu Cys Gln Ile Leu Arg Ala Leu Lys Leu Lys
     95                 100                 105 ttcaattctt ccttccttgt cattcttaaa ttcatttgta gtgacgattt tcctctttc    1711 tgtttatagt a ttg tgg att ttt tta aag agt tac ctc agt ttg tgg tca   1761
             Leu Trp Ile Phe Leu Lys Ser Tyr Leu Ser Leu Trp Ser
                          110                 115 agg ctg gat ctg tac tgg gtg aac ttt acg gcg cag act ggg aga aca    1809
Arg Leu Asp Leu Tyr Trp Val Asn Phe Thr Ala Gln Thr Gly Arg Thr
120                 125                 130                 135 gac ttc ag  gttttgacta acatctttta aatatacttc tacttctatt            1857
Asp Phe Arg atatcattgt taaatatgct tctattaact aattttact tacta g gca aag gag     1912
                                                   Ala Lys Glu
                                                           140 gtg cag gct aac ttt gtg cat ctt agc ctt cta agc aag tgagtttagc     1961
Val Gln Ala Asn Phe Val His Leu Ser Leu Leu Ser Lys
                145                 150 tcccttccta ttttacattt atctttgttt tgtgtaagaa tagttattga catagatttc   2021
atattttgga cctgcaactt agaagcaaat tttcttccta tgcaataatc agaatatggg   2081
cttgcaatat tccttccatt ttaaattaat taagatttag agttacagat ttctggtttt   2141
catgtgatta tattctgtga attgttttaa ggacatgtta agtatgatg ttttggtac    2201 ctttccttgg taaca gat act aca aac gtg ggt tcc ggg aat tct ttt tga  2252
                 Asp Thr Thr Asn Val Gly Ser Gly Asn Ser Phe
                              155                 160                 165 cat atg atg caa acg cag aaa aga act cag caa act ctt cta cct att    2300
His Met Met Gln Thr Gln Lys Arg Thr Gln Gln Thr Leu Leu Pro Ile
                170                 175                 180 tgc tgg ata gtt atc gtt ttg gat ggc tac tct ttt tgg cac tcc gaa    2348
Cys Trp Ile Val Ile Val Leu Asp Gly Tyr Ser Phe Trp His Ser Glu
                185                 190                 195 acc atg cgt tta gtc gat tta agg acc tcg tga cat gct caa atg gcg    2396
Thr Met Arg Leu Val Asp Leu Arg Thr Ser     His Ala Gln Met Ala
200                 205                         210 tag ttt cta tat t ggttagtgac tacctgtgga gctctcccta atctttcatt      2449
    Phe Leu Tyr
            215 cattttagtc ttgctgtaca ttattacttg aaagatgctt cgtttaatat aacgcaattg  2509 aagtataggc taactccttt tcatgttatc a gg  cta ttt tga tca tac atg    2560
                                       Trp Leu Phe     Ser Tyr Met
                                                                220 ttc ctt gtc ggt tta gaa att tca gca tcc aag att ctt ctc gct t      2606
Phe Leu Val Gly Leu Glu Ile Ser Ala Ser Lys Ile Leu Leu Ala
                225                 230                 235 tggtgagtgt ttatcttttc ttctatcccg ataaccatgg caccatagaa tgtttatcat   2666
ctattttcat ttatgtgatg aatctca gt  taa gaa agg tga caa agg tgt aga  2719
                              Cys     Glu Arg     Gln Arg Cys Arg
                                                          240 ctt ggt tgc atc act ttg caa gat ata tga cgc ctc aga aga tga gtt    2767
Leu Gly Cys Ile Thr Leu Gln Asp Ile     Arg Leu Arg Arg     Val
245                 250                 255 gag gat agt aat tga caa ggc aaa taa ttt ggt aga aac cat act gaa    2815
Glu Asp Ser Asn     Gln Gly Lys     Phe Gly Arg Asn His Thr Glu
                260                 265                 270 gaa aaa gcc atc tcc agc atc tga gtg cca aac tga caa gct aga taa    2863
```

-continued

| | | | | | | | | | | | | |
|---|---|---|---|---|---|---|---|---|---|---|---|---|
| Glu | Lys | Ala | Ile | Ser | Ser | Ile | | Val | Pro | Asn | | Gln | Ala | Arg |
| | | | | 275 | | | | | 280 | | | | | |

```
tat tga ccc a ggttggtcta aaatcatttt ccttcttcaa ttaaagaatc     2913
Tyr     Pro
285 atgtgagttc attgaacagt tgcctgattg ttcttcgaat ctatatggtg ttttactgca  2973 ga  tgg ctt gac cta ctt tga gga ttt act gga aga gac gtc cat ctc   3020
    Arg Trp Leu Asp Leu Leu     Gly Phe Thr Gly Arg Asp Val His Leu
            290             295                 300 aac tag ctt aat tac act tga aaa gga tta cta tga tgg taa agg cga   3068
Asn     Leu Asn Tyr Thr     Lys Gly Leu Leu     Trp     Arg Arg
                305                 310 act tga tga gag ggt att cat caa tga aga gga tag ctt act tgg atc   3116
Thr             Glu Gly Ile His Gln     Arg Gly     Leu Thr Trp Ile
                    315                 320                     325 tgg aag ctt atc tgc agg agc tgt taa tat tac tgg tgt taa gag gaa   3164
Trp Lys Leu Ile Cys Arg Ser Cys     Tyr Tyr Trp Cys     Glu Glu
                330                     335 aat tga tgc ttt gag ctc acc tgc aag gac att tat aag ccc act ttc   3212
Asn     Cys Phe Glu Leu Thr Cys Lys Asp Ile Tyr Lys Pro Thr Phe
340                     345                     350 tcc tca taa gtc gcc tgc tgc taa gac aaa tgg tat tag cgg tgc tac   3260
Ser Ser     Val Ala Cys Cys     Asp Lys Trp Tyr     Arg Cys Tyr
355                     360                     365 caa gtt ggc agc aac acc agt gag cac agc aat gac aac tgc caa gtg   3308
Gln Val Gly Ser Asn Thr Ser Glu His Ser Asn Asp Asn Cys Gln Val
            370                 375                 380 gct cag gac tgt cat atc ccc gct tct gcc aaa acc ttc tcc tgg gtt   3356
Ala Gln Asp Cys His Ile Pro Ala Ser Ala Lys Thr Phe Ser Trp Val
385                 390                 395 gga aca ttt cct taa atc atg tga tag gga tat aac aaa tga cgt cac   3404
Gly Thr Phe Pro     Ile Met     Gly Tyr Asn Lys     Arg His
400                     405                         410 acg aag agc aca cat aat att gga agc tat ttt ccc aaa tag ttc cct   3452
Thr Lys Ser Thr His Asn Ile Gly Ser Tyr Phe Pro Lys     Phe Pro
            415                 420                 425 tgg tgc cca atg tgg agg tgg aag ttt gca agc tgt tga cct gat gga   3500
Trp Cys Pro Met Trp Arg Trp Lys Phe Ala Ser Cys     Pro Asp Gly
            430                 435                 440 tga cat atg ggc aga gca gcg cag att aga agc ttg taa gtt ata cta   3548
    His Met Gly Arg Ala Ala Gln Ile Arg Ser Leu     Val Ile Leu
                445                 450                     455 cag agt tct tga ggc aat gtg taa agc aga agc tca gat ttt gca tgc   3596
Gln Ser Ser     Gly Asn Val     Ser Arg Ser Ser Asp Phe Ala Cys
                460                 465 aaa taa tct gaa ctc ttt att gac aaa tga gag gtt cca tag atg cat   3644
Lys     Ser Glu Leu Phe Ile Asp Lys     Glu Val Pro     Met His
470                     475                 480 gct tgc ttg ctc agc tga att ggt act ggc tac cca caa aac aat tac   3692
Ala Cys Leu Leu Ser     Ile Gly Thr Gly Tyr Pro Gln Asn Asn Tyr
            485                 490                 495 aat gtt gtt ccc agc tgt tct gga gag gac tgg gat cac agc ctt tga   3740
Asn Val Val Pro Ser Cys Ser Gly Glu Asp Trp Asp His Ser Leu
            500                 505                 510 tct cag caa ggt aat tga gag ttt cat acg aca tga aga ttc tct gcc   3788
Ser Gln Gln Gly Asn     Glu Phe His Thr Thr     Arg Phe Ser Ala
            515                 520                     525 tag aga gtt gag acg aca tct gaa ttc act gga gga acg gct tct aga   3836
    Arg Val Glu Thr Thr Ser Glu Phe Thr Gly Gly Thr Ala Ser Arg
```

-continued

| | | |
|---|---|---|
| 530 | 535 | 540 | gag tat ggt atg gga gaa agg ctc ttc aat gta caa ttc tct gat tgt    3884
Glu Tyr Gly Met Gly Glu Arg Leu Phe Asn Val Gln Phe Ser Asp Cys
            545                 550                 555 tgc cag gcc atc gct tgc att gga gat aaa tca gct cgg ttt act agc    3932
Cys Gln Ala Ile Ala Cys Ile Gly Asp Lys Ser Ala Arg Phe Thr Ser
            560                 565                 570 tga acc aat gcc atc tct gga tgc aat cgc agc act tat taa ttt ctc    3980
    Thr Asn Ala Ile Ser Gly Cys Asn Arg Ser Thr Tyr     Phe Leu
            575                 580                 585 tga cgg agc aaa tca tgc atc atc tgt aca aaa gca tga aac ttg tcc a  4029
    Arg Ser Lys Ser Cys Ile Ile Cys Thr Lys Ala     Asn Leu Ser
            590                 595                 600 ggtagtttta tttgtttctg aattaaagca gttttccaac ctgctgttaa tggtatgatt   4089
ttcttaccaa aaattgtcaa atttgctgcc atata gg  aca aaa tgg ggg gat     4141
                                          Arg Thr Lys Trp Gly Asp
                                                          605 tag atc gcc caa aag att atg tac tga tta ccg cag cat tct agt tga    4189
    Ile Ala Gln Lys Ile Met Tyr     Leu Pro Gln His Ser Ser
            610                 615                 620 acg caa ttc ctt tac atc acc agt aaa gga tcg tct gtt ggc ctt agg    4237
Thr Gln Phe Leu Tyr Ile Thr Ser Lys Gly Ser Ser Val Gly Leu Arg
            625                 630                 635 caa cgt taa atc caa gat gct gcc acc tcc gtt gca gtc tgc att tgc    4285
Gln Arg     Ile Gln Asp Ala Ala Thr Ser Val Ala Val Cys Ile Cys
                640                 645                 650 ca  ggtacatttt gagtaactat gagtagaaat ggagagttag tttacctatc         4337
Gln tagttgtccc tgtacttgtt aagtaacctc ttcggattta tgtctaca g ccc aac     4392
                                                        Pro Asn acg gcc caa ccc agg agg tgg agg aga aac ttg tgc aga aac tgg aat    4440
Thr Ala Gln Pro Arg Arg Trp Arg Arg Asn Leu Cys Arg Asn Trp Asn
655                 660                 665                 670 caa tat ttt ctt cac aaa ggtaggtctg tgagatcttt ggatctacta           4488
Gln Tyr Phe Leu His Lys
                675 ctaatcgttt ggttagatga tgtactacaa aacacggtat tgattcttca ttttcggctg  4548 ggaattgtgt taaatgtggt ggctcttccc a gat taa taa att ggc tgc tgt     4600
                                    Asp         Ile Gly Cys Cys
                                                            680 aag aat caa tgg aat ggt gga aag act aca act ttc aca gca aat aag    4648
Lys Asn Gln Trp Asn Gly Gly Lys Thr Thr Thr Phe Thr Ala Asn Lys
            685                 690                 695 gga gag tgt gta ttg ttt ctt cca aca tgt act tgc tca gcg gac ttc    4696
Gly Glu Cys Val Leu Phe Leu Pro Thr Cys Thr Cys Ser Ala Asp Phe
            700                 705                 710 tct ttt att cag tcg aca cat tga cca gat cat tct ctg ttg ctt cta    4744
Ser Phe Ile Gln Ser Thr His     Pro Asp His Ser Leu Leu Leu Leu
            715                 720                 725 cgg agt ggc caa ggtgagtagt gtgattcaaa gggtttaact atatgtcatc        4796
Arg Ser Gly Gln
        730 tggtttacaa tggcttctct tacacttaca ctttttccat gaatcacctt gtagatatcc  4856 caaatgagcc tga ctt tca ggg aaa tca tat aca act acc gga agc aac     4905
                Leu Ser Gly Lys Ser Tyr Thr Thr Thr Gly Ser Asn
                                735                 740 cac agt gta aac cat tag ttt tcc gca gcg ttt atg tgg atg cgt tac    4953

-continued

```
His Ser Val Asn His     Phe Ser Ala Ala Phe Met Trp Met Arg Tyr
745                 750                 755 aat gtc gcc gtc aag g ggtatatata cactcttaac cttatgctga aagtttctt      5009
Asn Val Ala Val Lys
760 tactcggtgg agaagactaa atttgtgaca atgacttgaa ca ga  gaa tag ggc        5062
                                                  Gly Glu     Gly cag atc atg ttg aca tca tca cat tct aca atg aaa tat tta ttc ctg       5110
Gln Ile Met Leu Thr Ser Ser His Ser Thr Met Lys Tyr Leu Phe Leu
        770                 775                 780 ccg taa agc cgc tgc tgg tgg agc tag gtc ctg taa gaa acg acc ggg       5158
Pro     Ser Arg Cys Trp Trp Ser     Val Leu     Glu Thr Thr Gly
            785                 790                         795 ctg tgg aag cca ata ata agc ctg aa  ggtagttaag aaaggccaga             5204
Leu Trp Lys Pro Ile Ile Ser Leu Lys
                800 tacttgttag atgtaagctt tgtctatcaa tttagtccct aagttaaatg atcgtcttat     5264 tttggattca ca g gtc aat gtc ccg gat cgc caa agg tgt ctg tgt ttc       5313
                 Val Asn Val Pro Asp Arg Gln Arg Cys Leu Cys Phe
                                     810                 815 caa gtg ttc cag aca tgt ccc cta aaa aag tat ctg cag tgc aca atg       5361
Gln Val Phe Gln Thr Cys Pro Leu Lys Lys Tyr Leu Gln Cys Thr Met
        820                 825                 830 ttt atg ttt ctc ctc ttc ggg gat caa ag  gtaaagaaga tcatagtgct         5410
Phe Met Phe Leu Leu Phe Gly Asp Gln Arg
        835                 840 taactcttta tcatgatatg actaagtctt gaggaggagg taggtgacaa gattgtttgg     5470
ttaccttcca tgtgttgtgt gtttgca g atg gat gct ctt att tca cac agt      5522
                                Met Asp Ala Leu Ile Ser His Ser
                                                    845         850 aca aag agt tac tat gct tgt gtt gga gag agt aca cat gct tac cag       5570
Thr Lys Ser Tyr Tyr Ala Cys Val Gly Glu Ser Thr His Ala Tyr Gln
        855                 860                 865 agc cct tca aag gac cta tct gcc atc aac aac cgc ttg aac a             5613
Ser Pro Ser Lys Asp Leu Ser Ala Ile Asn Asn Arg Leu Asn
        870                 875                 880 agtaagtaaa aaaatcacgt ctctcatcag cttcttccat aaaaccaatc actgacccaa     5673
tccaatttca tctggtgtca ca gc  agc agc agc aac cgc aag agg acg cta      5724
                             Ser Ser Ser Asn Arg Lys Arg Thr Leu
                                     885                 890 aac ttt gac gca gaa gca ggg atg gtc agc gat tcc atg gta gca aat       5772
Asn Phe Asp Ala Glu Ala Gly Met Val Ser Asp Ser Met Val Ala Asn
        895                 900                 905 agc ctt aac ctc caa aac caa aat caa aac caa aat gga agc gat gca       5820
Ser Leu Asn Leu Gln Asn Gln Asn Gln Asn Gln Asn Gly Ser Asp Ala
        910                 915                 920 tcg tcc tca ggt ggt gcc gca ccc ctt aaa acc gag cca aca gat tca       5868
Ser Ser Ser Gly Gly Ala Ala Pro Leu Lys Thr Glu Pro Thr Asp Ser
    925                 930                 935 ta gatatctctc tctacttgct acaccaactt ctcttcagtt atagcatctg             5920
taaatcctta tgttgcagag tttgcttttta tgtttagctt tctagtttat agtgatcacc    5980
tcaggctatg agcggatgga tcccttattt gtttctttt tctttttttta tcttagttaa     6040 gtcagtctta ataagcatta ataaatgtct ttttcttgtt cactctttct aactgtgttc     6100
ggtgtcccat ctactaaatt tatttttccac tttaaaaaaa aacaatttgt gacatttact    6160
taacttggaa catatacagt acagttaagc aattaactat aaccaacaaa ttgtctgaac     6220
```

```
aattgtctgt cttacctttt tagctctcta taaatttacg ccgcaaaaca acactttatg    6280
tcgatttcag aataacttac tactccagca tatttctcaa aactttctca ataggttaaa    6340
tttaaaacaa ccttgcaact tatgaaaaaa tcctccagca aatttgccag aaaagaatgt    6400
tacaatggct acaatcacat cc                                              6422
```

US 7,164,006 B1

ALTERATION OF PLANT MERISTEM FUNCTION BY MANIPULATION OF THE RETINOBLASTOMA-LIKE PLANT RRB GENE

CROSS-REFERENCE TO RELATED APPLICATIONS

This application is a continuation of U.S. Non-provisional application Ser. No. 09/527,084 filed Mar. 16, 2000, now U.S. Pat. No. 6,696,560, which claims the benefit of U.S. Provisional Application No. 60/125,229 filed Mar. 19, 1999, both of which are hereby incorporated herein by this reference. Reference is made to co-pending U.S. non-provisional application Ser. No. 10/748,912, filed Dec. 11, 2003, which is hereby incorporated herein by this reference, which is a divisional of U.S. Non-provisional application Ser. No. 09/527,084 filed Mar. 16, 2000, currently pending, which claims the benefit of U.S. Provisional Application No. 60/125,229 filed Mar. 19, 1999. Reference is made to co-pending U.S. non-provisional application Ser. No. 29/101,943, filed Mar. 15, 1999, which is hereby incorporated herein by this reference, which is a continuation of U.S. Non-provisional application Ser. No. 09/527,084 filed Mar. 16, 2000, currently pending, which claims the benefit of U.S. Provisional Application No. 60/125,229 filed Mar. 19, 1999.

STATEMENT REGARDING FEDERALLY SPONSORED RESEARCH OR DEVELOPMENT

The United States Government has rights in this invention pursuant to Grant No. MCB9506985, between the National Science Foundation and the University of California, and Grant No. DE-FG03-88ER13882 between the U.S. Dept. of Energy and the University of California.

REFERENCE TO A "SEQUENCE LISTING", A TABLE, OR A COMPUTER PROGRAM LISTING APPENDIX SUBMITTED ON A COMPACT DISC (SEE 37 CFR 1.52(E)(5))

Not Applicable

BACKGROUND OF THE INVENTION

1. Field of the Invention

The present invention relates generally to modulating the growth, differentiation and/or cell division of meristematic cells in a plant, more particularly modulating said cells via modulating RRB gene activity.

2. Description of Related Art

The ability to control the size of plants and plant tissues is an enormously valuable tool. For example, for many agricultural crops, increasing the size of a plant or of a specific tissues within a plant would be of obvious commercial value. Currently, most attempts to increase plant size or yield are accomplished through traditional or marker-assisted breeding programs. Such methods have, however, failed to provide methods to directly control the size of plants or plant tissues.

Most cell proliferation in plants occurs in tissues called meristematic tissue. Several types of meristematic tissue exist in plants, including the shoot apical meristem, which gives rise to all aerial parts of the plant, the root apical meristem, which establishes the root system, and the vascular meristem, which provides lateral growth of the plant.

While several genes are known to alter meristem fate, and thereby plant development, the mechanism by which they function is poorly understood. The products of the CLAVATA (CLV) and SHOOT MERISTEMLESS (STM1) genes of *Arabidopsis*, for example, encoding a receptor-kinase and homeodomain protein, respectively, appear to work antagonistically in a shoot meristem maintenance pathway involved in the partitioning of the central-peripheral zone (CZ-PZ) of the meristem. Other genes, such as ZWILLE (ZLL) and WUSCHEL (WUS), function early in embryonic development to specify the stem cells which will be maintained in the central zone of the shoot apical meristem. Other genes such as MGOUN1(MGO1) and MGOUN2 (MG02) appear to function in the partitioning of cells from the PZ of the shoot apical meristem to leaf primordia or the inflorescence, often resulting in a fasciated meristem phenotype.

Plants containing mutations in the genes described above are defective in specific stages of meristem function and have well-characterized developmental phenotypes. As such, these genes are likely involved in the differentiation of meristematic cells, and are thus unlikely, by themselves, to provide tools to increase the size of plants or of plant tissues. Instead, it would be desirable to manipulate both the differentiation of meristematic cells as well as their growth and proliferation.

One potential method to alter the growth and/or proliferation of plant cells would be to modulate the activity of genes controlling these processes. For example, several groups have reported the cloning of at least a fragment of a Retinoblastoma-related protein in maize. See, e.g. Ach et al. (1997) Mol. Cell. Biol. 17:5077; Huntley et al. (1998) *Plant Mol. Biol.* 37:155; Grafi et al. (1996) *PNAS* 93:8962; Shen et al. (1994) Plant Mol. Biol. 26:1085; Xie et al. (1996) EMBO J 15:4900; and WO 97/47745. None of these studies, however, has investigated the function of RRB in proliferating, virus-free cells. Further, no studies have heretofore addressed the role of RRB in an intact plant. As well known to those of skill, only by examining the role of a protein in its normal environment, in an intact organism, can its true activity and/or function be determined.

Thus, the art lacks a good understanding of the function of RRB in plant cells and/or intact plants. Without this understanding, its use to control plant growth in an efficient manner is difficult if not impossible. The present invention addresses these and other needs.

BRIEF SUMMARY OF THE INVENTION

This invention provides methods and compositions for altering the growth and differentiation of plant tissues. The invention is based on the discovery that, in plants, genetically altering the levels of Retinoblastoma-related gene (RRB) activity produces dramatic effects on the growth, proliferation, and differentiation of plant meristem. Altering the level of RRB activity in a plant tissue, therefore, can be used to specifically control the growth and/or differentiation of plant meristem, thereby controlling, e.g. the relative size and distribution of individual tissues in a plant.

In certain embodiments, this invention provides polynucleotides and polypeptides with plant RRB function. In one embodiment, the polynucleotide is as shown in SEQ ID NO: 1 or SEQ ID NO: 9. In one embodiment, the polynucleotide encodes the polypeptide shown as SEQ ID NO:2, or fragments thereof. In a preferred embodiment, the polynucleotide encodes a full-length RRB protein. However, truncated forms of RRB proteins can be used as well. In addition, mutated forms of the RRB proteins can be used, e.g. as dominant negative forms.

This invention also provides transgenic plants comprising RRB polynucleotides. In preferred embodiments, the RRB polynucleotides are operably linked to a promoter, such as an inducible or tissue-specific promoter.

This invention also provides methods for inhibiting or enhancing the growth of plant cells, plant tissues, or entire plants. In preferred embodiments, RRB activity is enhanced or inhibited in a plant tissue by expressing a wild type, mutant, or truncated form of an RRB polynucleotide, or by expressing an inhibitor of RRB activity, e.g. a peptide that competitively binds RRB, thereby preventing its normal interaction with intracellular substrates.

The methods provided herein can also be used to alter the differentiation of a plant tissue. In preferred embodiments, the differentiation of a meristem is altered. For example, the present invention provides methods for modulating the RRB activity in an apical shoot meristem, thereby altering the size, organization, and/or differentiation of the meristem and, as a result, affecting the structure and/or number of, e.g., a leaf primordium or an inflorescence bolt. Increasing or decreasing RRB activity can be effected in a plant, a plant tissue, or a plant cell by expressing a wild type, mutant, or truncated form of an RRB polynucleotide, or by expressing a peptide inhibitor of RRB activity. Such RRB polynucleotides are preferably linked to promoters such as a tissue-specific or an inducible promoter.

DEFINITIONS

A "nucleic acid" refers to a single or double-stranded polymer of deoxyribonucleotide or ribonucleotide bases. The term includes chromosomal DNA, self-replicating plasmids, infectious polymers of DNA or RNA and DNA or RNA that performs a primarily structural role. With respect to a naturally occurring nucleic acid that is "isolated" from its natural environment, the nucleic acid is substantially or essentially free from components which normally accompany or interact with it as found in its naturally occurring environment. However, an "isolated" nucleic acid can refer to a recombinantly or synthetically produced nucleic acid, that is identical or altered from the naturally occurring nucleic acid sequence. In addition, an "isolated nucleic acid" can comprise naturally occurring nucleotides or can comprise any nucleotide derivative or analog, e.g. labeled nucleotides, that can be incorporated into a polynucleotide chain. Any aspect of the polynucleotide chain can be altered, such as the base, sugar, or phosphate backbone.

The term "promoter" refers to regions or sequence located upstream and/or downstream from the start of transcription and which are involved in recognition and binding of RNA polymerase and other proteins to initiate transcription. A "plant promoter" is a promoter that works in plants, e.g. CaMV 35S. A "tissue-specific promoter" is a promoter capable of initiating transcription in a certain tissue of a plant. A "tissue specific promoters" can comprise a naturally occurring promoter that drives the expression of a gene in one or more specific tissues, or can comprise modified, truncated, or otherwise modified derivatives of naturally occurring promoters, or can comprise a synthetic promoter with the desired properties. A "tissue specific promoter" can drive the expression of a gene in one or more tissues, and throughout the entire tissue or only in a subset of the tissue. In addition, a "tissue-specific promoter" can drive gene expression in a tissue throughout the life of a plant, or transiently at one or more times during the life of the plant.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

As used herein, the term "RRB polynucleotide" refers to any polynucleotide encoding a polypeptide with RRB activity, and which encodes a polypeptide with at least about 50% sequence identity to the exemplified sequences provided herein. The RRB polypeptides encoded by RRB polynucleotides have at least about 50%, 60%, 70%, 80%, 90% or higher sequence identity at the deduced amino acid level relative to the exemplary RRB polynucleotide sequences provided herein. "RRB polynucleotide" includes reference to nucleic acids of at least about 20, 30, 40, or 50 nucleotides in length, more preferably about 100, 200, 500, 1000, 2000, 5000 or more nucleotides. Thus, an "RRB polynucleotide" can be an RRB gene or a subsequence thereof.

"RRB activity" refers to one or more biochemical or genetic properties of an RRB polynucleotide or polypeptide. For example, when expressed in cells or tissues of a plant, an RRB polynucleotide can affect the growth, proliferation, and/or differentiation of plant cells and tissues, resulting in the phenotypes described herein. In addition, RRB can bind to a number of heterologous proteins, such as E2F, D-type cyclins, or viral proteins such as large-T antigen or E1A, or the geminivirus protein RepA. Often, such proteins will bind RRB through an LXCXE motif. Accordingly, RRB activity can be assessed based on binding to any LXCXE-motif containing polypeptide. Any of these activities, inter alia, can be monitored or modified according to the present invention.

An "inhibitor of RRB activity", as used herein, refers to any material that results in the decrease of RRB activity. Such molecules can include expressible forms of RRB polynucleotides, such as antisense RRB polynucleotides, RRB polynucleotides used to inhibit by co-suppression, dominant-negative forms of RRB such as truncated or mutated forms of RRB, as well as other expressible inhibitors such as peptide inhibitors of RRB or anti-RRB ribozymes. In addition, an "inhibitor of RRB activity" can include any material that can be used to decrease RRB activity, such as molecules that inhibit the activity, expression, or stability of RRB polynucleotides or polypeptides.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectations (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

| | |
|---|---|
| 1) | Alanine (A), Serine (S), Threonine (T); |
| 2) | Aspartic acid (D), Glutamic acid (E); |
| 3) | Asparagine (N), Glutamine (Q); |
| 4) | Arginine (R), Lysine (K); |
| 5) | Isoleucine (I), Leucine (L), Methionine (M), Valine (V); and |
| 6) | Phenylalanine (F), Tyrosine (Y), Tryptophan (W). |

(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising RRB nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency. In preferred embodiments, stringent hybridization conditions for screening cDNA libraries and/or for Southern blot hybridizations include:

Hybridization at 55° C. in the following:
  0.75M NaCl
  5 mM EDTA pH 8
  0.15M Tris HCl pH 8
  2.75 mM tetra sodium pyrophospate
  0.1% Ficoll
  0.1% polyvinyl pyrrolidone
  0.1% BSA
  10% Dextran sulphate
  0.1% SDS
  0.05 mg/ml herring sperm DNA
  Washing in 2×SSC, 0.1% SDS at 55° C., using, e.g. an RRB cDNA as a probe for hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

BRIEF DESCRIPTION OF THE SEVERAL VIEWS OF THE DRAWING

Not Applicable

DETAILED DESCRIPTION OF THE INVENTION

This invention provides methods of directly controlling the size and/or differentiation state of plants, plant tissues, or plant cells. This invention is based on the surprising discovery that, in intact plants, alterations in RRB levels dramatically affect the growth, organization, as well as differentiation of specific tissues. By specifically increasing or decreasing the level of RRB in cells within an intact plant, therefore, it is possible to increase or decrease the size of the tissue or plant comprising the cells. When directed to specific tissues within a plant, it is thus possible to specifically and controllably alter the growth and/or differentiation of the tissue.

I. RRB

Any of a number of RRB sequences can be used in the present invention. RRB sequences can be used from any monocotyledonous or dicotyledonous plant, such as *Arabidopsis, Zea mays, Chenopodium*, and tobacco. In addition, RRB homologs from animals, such as from mammals, fish, birds, insects, etc. can be used. In preferred embodiments, an RRB nucleotide sequence will be used that will hybridize, under low to moderate stringency, to SEQ ID NO:1, 3, 5, 7, or 9, or which is substantially identical to all or part of SEQ ID NO:1, 3, 5, 7, or 9. Also preferred is the use of RRB polypeptides substantially similar to all or part of SEQ ID NO:2, 4, 6, or 8. The present invention can be used with full-length, truncated, wild type, or mutated forms of RRB, as described infra.

Typically, the RRB sequences will include one or more functional domains characteristic of RRB sequences, such as the A or B pocket, one or more protein or protein-motif binding domains, e.g. an LXCXE motif binding domain, and phosphorylation sites. In addition, the N-terminal 130 amino acids, or 383 5' nucleotides, of the *Arabidopsis* sequence, which are not found in *Zea mays*, can be used. Such *Arabidopsis*-specific sequences can readily be identified by comparing an *Arabidopsis* sequence, e.g. SEQ ID NO:1, with, e.g. a *Zea mays* sequence as shown in SEQ ID NO:3, 5, or 7. RRB sequences can be isolated from any natural source, can be derived from a natural source, i.e. a mutated or truncated derivative, or can be synthesized de novo. Methods for purifying, mutating, and recombinantly altering nucleic acids are well known in the art, and can be found in any of a multitude of guides, such as Sambrook et al., (1989) and Ausubel et al. (1999).

II. Altering RRB Expression and/or Activity in Plant Tissues

The present invention can be used to alter the growth, organization, and/or differentiation of any of a number of plant tissues. Typically, the tissues will comprise meristematic tissue, including root meristem, shoot apical meristem, vascular meristem, or endosperm. In certain embodiments, RRB activity may be modulated in non-meristematic tissue, e.g. to affect the differentiation of the tissue or, e.g. to promote proliferation in normally non-proliferating cells. Accordingly, the present methods can be used to affect the growth and/or differentiation of any part of a plant, including roots, stems, leaves, flowers, seed, fruit, tubers etc., as well as any structure within one of these parts, e.g. bracts, sepals, petals, stamens, carpels, anthers, ovules, embryos, endosperm, and seed coat).

Any of these tissues can be targeted individually or in combination, e.g. using one or more tissue specific promoters such as leaf-specific promoters, flower meristem-specific promoters, endosperm-specific promoters, root-specific promoters, etc. Also, the tissues can be targeted at all times during the life of the plant, e.g. using a constitutive promoter, or transiently, e.g. using a transiently active or an inducible promoter. It will be appreciated that, e.g. using multiple expression constructs, RRB activity can be simultaneously increased in one tissue and decreased in another in a single plant, thereby altering the relative sizes of the tissues within a plant. For commercial crops, such methods would allow the relative increase in the yield of valuable tissues, and the decrease in size of unwanted tissues.

These methods can be used to enhance and/or inhibit the growth and differentiation of plant cells. Further, we have discovered a relationship between the amount of increase or decrease in the level of RRB activity and the degree to which growth, organization, and/or differentiation is affected. For example, in a transgenic plant with an RRB polynucleotide under the control of an inducible promoter, adding a small amount of the inducing agent results in a mild effect on growth, organization, and/or differentiation, whereas adding a substantial amount of the agent results in dramatic changes in the rate or level of growth, organization and/or differentiation. Accordingly, the present invention can be used to alter the degree to which a plant tissue grows, organizes, and/or differentiates, e.g. by using a variable amount of an inducing agent or by using promoters of various strengths.

In certain embodiments, the level of RRB activity will be altered alone, i.e. no other cellular moieties will be manipulated. In other embodiment, however, RRB levels can be altered in conjunction with other cellular components. For example, other regulators of cell growth, cell proliferation, or cellular differentiation may be altered to enhance or attenuate the effects of the altered RRB levels. In certain embodiments, genes involved in meristem formation and/or differentiation may be used, e.g. CLV, STM1, ZLL, WUS, MGO1, or MGO2. For example, a gene promoting meristem formation may be used to increase the amount of meristem, which can be increased further by, e.g. modulating the levels of RRB in the meristem. Finally, the enlarged meristem can subsequently be induced to differentiate by further altering RRB activity in the cells.

A. Increasing RRB Activity or RRB Gene Expression

Any of a number of means well known in the art can be used to increase RRB activity in plants. Increased RRB activity can be used to, e.g. modulate the growth of plant tissues, modulate the organization of plant tissues, and/or modulate the differentiation of the tissues. In a preferred embodiment, increasing RRB activity in cells within a plant or a plant tissue results in a decrease in the size of the plant or plant tissue. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or more RRB genes can be expressed constitutively (e.g., using a constitutive promoter).

1. Increasing Expression of RRB Polynucleotides

Isolated sequences prepared as described herein can be used to introduce expression of a particular RRB nucleic acid to increase gene expression using methods well known to those of skill in the art. Preparation of suitable constructs and means for introducing them into plants are described below.

One of skill will recognize that the polypeptides encoded by the genes of the invention, like other proteins, have different domains that perform different functions. Thus, the gene sequences need not be full length, so long as the desired functional domain of the protein is expressed. For example, RRB can bind to various proteins, such as E2F, D-type cyclins, E1A, large T-antigen, and other viral proteins, and has multiple conserved domains, such as the A and B pocket domains and conserved phosphorylation sites. Any of these binding sites or conserved regions may be used in the present invention.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

In certain embodiments, modified forms of RRB will be used that have increased RRB activity in vivo. For example, creating forms of RRB that cannot be inhibited by phosphorylation will create a hyperactive form of RRB. Additional hyperactive forms can be readily identified, e.g. by screening for modified forms of RRB with an enhanced ability to inhibit the cell cycle or to promote differentiation.

RRB polynucleotide expression can be increased throughout a plant, in one or more tissues or cells of a plant, and constitutively or transiently. Such expression patterns can be achieved using any of a variety of promoters, including endogenous RRB promoters, heterologous promoters, constitutive promoters, tissue-specific promoters, and inducible promoters.

2. Modification of Endogenous RRB Genes to Increase RRB Activity

In certain embodiments of this invention, endogenous RRB will be targeted for modification. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Alternatively, homologous recombination can be used to induce targeted gene modifications by specifically targeting the RRB gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an RRB gene sequence (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered RRB gene expression in transgenic plants. The mutated gene will interact with the target wild-type gene in such a way that homologous recombination and targeted replacement of the wild-type gene will occur in transgenic plant cells, resulting in increased RRB activity.

Alternatively, oligonucleotides composed of a contiguous stretch of RNA and DNA residues in a duplex conformation with double hairpin caps on the ends can be used. The RNA/DNA sequence is designed to align with the sequence of the target RRB gene and to contain the desired nucleotide change. Introduction of the chimeric oligonucleotide on an extrachromosomal T-DNA plasmid results in efficient and specific RRB gene conversion directed by chimeric molecules in a small number of transformed plant cells. This method is described in Cole-Strauss et al., *Science* 273: 1386–1389 (1996) and Yoon et al. *Proc. Natl. Acad. Sci. USA* 93: 2071–2076 (1996).

3. Other Means for Increasing RRB Activity

One method to increase RRB expression is to use "activation mutagenesis" (see, e.g. Hiyashi et al. *Science* 258: 1350–1353 (1992)). In this method an endogenous RRB gene can be modified to be expressed constitutively, ectopically, or excessively by insertion of T-DNA sequences that contain strong/constitutive promoters upstream of the endogenous RRB gene. As explained below, preparation of transgenic plants overexpressing RRB can also be used to increase RRB expression. Activation mutagenesis of the endogenous RRB gene will give the same effect as overexpression of the transgenic RRB nucleic acid in transgenic plants. Alternatively, an endogenous gene encoding an enhancer of RRB activity or expression of the endogenous RRB gene can be modified to be expressed by insertion of T-DNA sequences in a similar manner and RRB activity can be increased.

Another strategy to increase RRB expression can involve the use of dominant hyperactive mutants of RRB by expressing modified RRB transgenes. For example expression of modified RRB with a defective domain that is important for interaction with a negative regulator of RRB activity can be used to generate dominant hyperactive RRB proteins. Alternatively, expression of truncated RRB proteins which have only a domain that interacts with a negative regulator can titrate the negative regulator and thereby increase endogenous RRB activity. Use of dominant mutants to hyperactivate target genes is described, e.g., in Mizukami et al. *Plant Cell* 8:831–845 (1996).

B. Inhibition of RRB Activity or Gene Expression

As explained above, RRB activity is important in controlling the growth and differentiation of cells. Inhibition of RRB gene expression activity can be used, for instance, to alter cell growth and/or proliferation, to modulate tissue organization, and/or to modulate differentiation of cells within a tissue or plant. In a preferred embodiment, decreasing RRB activity in cells of a plant or a plant tissue results in an increase in the size of the plant or plant tissue. In particular, targeted expression of RRB nucleic acids that inhibit endogenous gene expression (e.g., antisense or co-suppression) can be used.

1. Inhibition of RRB Gene Expression

The nucleic acid sequences disclosed herein can be used to design nucleic acids useful in a number of methods to inhibit RRB or related gene expression in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque *Plant Sci.* (Limerick) 105: 125–149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. pp. 181–238; Heiser et al. *Plant Sci.* (*Shannon*) 127: 61–69 (1997)) and by preventing the accumulation of mRNA which encodes the protein of interest, (see, Baulcombe *Plant Mol. Bio.* 32:79–88 (1996); Prins and Goldbach *Arch. Virol.* 141: 2259–2276 (1996); Metzlaff et al. *Cell* 88: 845–854 (1997), Sheehy et al., *Proc. Nat. Acad. Sci. USA*, 85:8805–8809 (1988), and Hiatt et al., U.S. Pat. No. 4,801,340).

The nucleic acid segment to be introduced generally will be substantially identical to at least a portion of the endogenous RRB gene or genes to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress RRB gene expression. The targets can include, for instance, the coding regions, introns, sequences from exon/intron junctions, 5' or 3' untranslated regions, and the like.

Another well-known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al. *Plant Mol. Bio.* 22: 1067–1085 (1993); Flavell *Proc. Natl. Acad. Sci. USA* 91: 3490–3496 (1994); Stam et al. *Annals Bot.* 79: 3–12 (1997); Napoli et al., *The Plant Cell* 2:279–289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants that over-express the introduced sequence. A higher identity in a sequence shorter than full-length compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Oligonucleotide-based triple-helix formation can also be used to disrupt RRB gene expression. Triplex DNA can inhibit DNA transcription and replication, generate site-specific mutations, cleave DNA, and induce homologous recombination (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (Berlin) 75: 267–282 (1997)). Triple helix DNAs can be used to target the same sequences identified for antisense regulation.

Catalytic RNA molecules or ribozymes can also be used to inhibit expression of RRB genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation.

A number of classes of ribozymes have been identified. One class of ribozymes is derived from a number of small circular RNAs that are capable of self-cleavage and replication in plants. The RNAs replicate either alone (viroid RNAS) or with a helper virus (satellite RNAs). Examples include RNAs from avocado sunblotch viroid and the satellite RNAs from tobacco ringspot virus, lucerne transient streak virus, velvet tobacco mottle virus, *solanum* nodiflorum mottle virus and subterranean clover mottle virus. The design and use of target RNA-specific ribozymes is described in Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature,* 334:585–591 (1988).

2. Modification of Endogenous RRB Genes

Methods for introducing genetic mutations described above can also be used to select for plants with decreased RRB expression.

3. Other Methods for Inhibiting RRB Activity

RRB activity may be modulated by eliminating the proteins that are required for RRB cell-specific gene expression. Thus, expression of regulatory proteins and/or the sequences that control RRB gene expression can be modulated using the methods described here.

Another strategy is to inhibit the ability of a RRB protein to interact with itself or with other proteins. This can be achieved, for instance, using antibodies specific to RRB. In this method cell-specific expression of RRB-specific antibodies is used to inactivate functional domains through antibody:antigen recognition (see, Hupp et al., *Cell* 83:237–245 (1995)). Interference of activity of a RRB interacting protein(s) can be applied in a similar fashion.

Alternatively, dominant negative mutants of RRB can be prepared by expressing a transgene that encodes a truncated RRB protein. Use of dominant negative mutants to inactivate target genes in transgenic plants is described in Mizukami et al., *Plant Cell* 8:831–845 (1996). In a preferred embodiment, an RRB polypeptide with a mutation that prevents binding of RRB to heterologous proteins, e.g. a mutation in a conserved cysteine residue (corresponding to C706 of human RB), is expressed in a cell. With respect to the *Arabidopsis* cDNA shown as SEQ ID NO: 1, the alteration comprises a cysteine to phenylalanine substitution, resulting from a G to T change at position 2363 bp. In particularly preferred embodiments, such mutated or truncated RRB proteins are expressed at a level at least as high as that of the endogenous RRB protein.

Another approach to inhibit RRB activity is through the use of peptide inhibitors of RRB activity. Such inhibitors may be derived from naturally occurring proteins, e.g. RRB binding proteins. For example, a fragment of E2F that competitively binds RRB and prevents it from binding to full length E2F may be expressed in a cell. Also, a peptide include an LXCXE motif can be used, thereby competitively blocking the binding of proteins such as D-type cyclins to RRB. However, any peptide with the ability to inhibit RRB activity, by interacting directly with RRB itself or with a substrate of RRB, can be used. Such peptides can be easily identified, for example, by generating a library of peptide molecules and screening the library for peptides with the ability to bind to and/or inhibit RRB in vitro or in vivo.

In certain embodiments, a non-peptide inhibitor of RRB can be used. Such inhibitors can be any molecule or treatment that reduces RRB activity in a cell. Such molecules can include organic compounds including nucleic acids, nucleotides, amino acids, carbohydrates, fats, waxes, hormones, etc., or any inorganic compounds. Any compound can be screened for the ability to bind to and/or inhibit RRB activity, in vitro or in vivo. In addition, any non-molecular treatment, e.g. temperature, electromagnetic radiation, motion, etc. that affects RRB activity can be employed.

III. Isolation and Manipulation of RRB Polynucleotides and Polypeptides

A. Purification of RRB Polypeptides

Either naturally occurring or recombinant RRB polypeptides can be purified for use in functional assays, e.g. protein binding assays. Naturally occurring RRB polypeptides can be purified, e.g., from plant tissue and any other source of a RRB homolog. Recombinant RRB polypeptides can be purified from any suitable expression system.

The RRB polypeptides may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant RRB polypeptides are being purified. For example, proteins having established molecular adhesion properties can be reversible fused to the RRB polypeptides. With the appropriate ligand, the RRB polypeptides can be selectively adsorbed to a purification column and then freed from the column in a relatively pure form. The fused protein is then removed by enzymatic activity. Finally the RRB polypeptides could be purified using immunoaffinity columns.

B. Isolation of RRB Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of RRB nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library which contains a RRB gene transcript is prepared from the mRNA. Alternatively, cDNA may be prepared from mRNA extracted from other tissues in which RRB genes or homologs are expressed.

The cDNA or genomic library can then be screened using a probe based upon the sequence of a cloned RRB gene disclosed here. Probes may be used to hybridize with genomic DNA or cDNA sequences to isolate homologous genes in the same or different plant species. Alternatively, antibodies raised against a RRB polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of RRB genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: *A Guide to Methods and Applications*. (Innis, M, Gelfand, D., Sninsky, J. and White, T., eds.), *Academic Press*, San Diego (1990). Appropriate primers and probes for identifying RRB sequences from plant tissues are generated from comparisons of the sequences provided herein (e.g. SEQ ID NO: 1, SEQ ID NO:3, SEQ ID NO:5, SEQ ID NO:7, etc.).

Polynucleotides may also be synthesized by well-known techniques, as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

C. Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S and 19S transcription initiation regions; the full-length FMV transcript promoter (Gowda et al., *J Cell Biochem* 13D:301; the 1'- or 2'-promoter derived from T-DNA of *Agrobacterium tumafaciens*, and other transcription initiation regions from various plant genes known to those of skill. Such promoters and others are described, e.g. in U.S. Pat. No. 5,880,330. Such genes include for example, ACT11 from *Arabidopsis* (Huang et al. *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208: 551–565 (1989)), and Gpc2 from maize (GenBank No. U45855, Manjunath et al., *Plant Mol. Biol.* 33:97–112 (1997)).

Alternatively, the plant promoter may direct expression of RRB nucleic acid in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or sprayed with chemicals/hormones. Numerous inducible promoters are known in the art, any of which can be used in the present invention. Such promoters include the yeast metallothionine promoter, which is activated by copper ions (see, e.g. Mett et al. (1993) PNAS 90:4567), the dexamethasone-responsive promoter, In2–1 and In2–2, which are activated by substituted benzenesulfonamides, and GRE regulatory sequences, which are glucocorticoid-responsive.

Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can also be used in the invention. For instance, promoters that direct expression of nucleic acids in leaves, roots or flowers are useful for the growth, proliferation, and/or differentiation of those organs. For expression of a RRB polynucleotide in the aerial vegetative organs of a plant, photosynthetic organ-specific promoters, such as the RBCS promoter (Khoudi, et al., *Gene*

197:343, 1997), can be used. Root-specific expression of RRB polynucleotides can be achieved under the control of the root-specific ANR1 promoter (Zhang & Forde, *Science*, 279:407, 1998). Other suitable tissue specific promoters include the cdc2a and cyc07 promoters, the histone promoter, the cinnamyl alcohol dehydrogenase (CAD) promoter, the mustard CHS1 promoter, the bean grp 1.8 promoter, the PAL1 promoter, the chalcone synthase A promoter, the UFO promoter, and others. In preferred embodiments, a promoter will be used that drives RBB expression specifically in a meristem. In preferred embodiments, an RRB promoter will be used. For example, the RRB promoter shown in SEQ ID NO:9 (e.g. approximately base pairs 1–543) can be used to drive expression of operably linked sequences in meristematic and other tissues in *Arabidopsis* or any type of plant.

In addition, the promoter shown in SEQ ID NO:9 (e.g. approximately base pairs 1 to 543 or, e.g. 1–1000) can be used to drive the expression of heterologous genes in meristematic tissue. RRB promoters can be used to drive the expression of any heterologous gene whose expression in meristematic tissue is desired. For example, cell cycle-related genes such as cyclins, Cdks, E2F, DP, p53, Cdc25, CKIs, or any derivative or variation thereof, can be used, as can developmental genes such as CLV, STM1, ZLL, WUS, MGO1, or MGO2.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

IV. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Limm, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of RRB mRNA or protein in transgenic plants. Means for detecting and quantitating mRNAs or proteins are well known in the art.

EXAMPLES

The full-length *Arabidopsis thaliana* Rb (AtRRB) cDNA was cloned into plant expression cassettes behind a dexamethasone-inducible promoter (DEX-inducible plasmid pTA7002) to manipulate ectopic expression (AtRRB-OE) of the AtRRB gene. A mutated version of the AtRRB cDNA containing a cystidine to phenylalanine substitution resulting from a G to T change at position 2363 bp was also cloned into a plant expression cassette (AtRRBcys-OE). By analogy to metazoan Rb-like proteins, the protein encoded by AtRRBcys would be altered in structure and function and is predicted to act as a dominant negative mutation when ectopically expressed.

Numerous phenotypic alterations were observed in transgenic lines, including enlargement of the inflorescence bolt, or formation of multiple meristems at the shoot apex. Other phenotypic alterations include delayed leaf emergence, altered leaf morphology (with regard to degree of development, shape and fused organs), or terminal flower formation. A subset of transgenic lines show a complete loss of shoot and root apical meristem activity. Our results document a key role for the product of the plant RRB gene in meristem differentiation, organization, and the meristematic cell cycle. The plant RRB gene is therefore a key target for functional manipulations to alter cell cycle regulation, apportioning of cells to primordia, and cellular differentiation in shoot and root apical meristems.

Numerous phenotypes were observed in most of the transgenic lines in the uninduced condition, i.e. in the absence of dexamethasone (the DEX—inducible promoter system is known to be "leaky" in vivo). Phenotypes were typically enhanced following induction of the promoter with dexamethasone. These results demonstrate that we can modify expression of the transgenes and phenotypic responses. Of the different phenotypes obtained in the DEX-AtRRB-OE and DEX-AtRRBcys-OE transgenic lines, the most penetrant phenotypes observed are in the impaired ability of the meristem to (1) generate leaf primordia and (2) to maintain a proper size and/or organization, as observed by severely delayed leaf emergence and fasciation of the inflorescence bolt, respectively. These phenotypes are reminiscent o Arabidopsis thaliana mgo mutants, which have a similar phenotype including delayed emergence of leaves and an enlarged shoot apical meristem, observed as fasciation. These results suggest that one function of AtRRB is the removal of cells from the PZ of the shoot apical meristem and in the differentiation of the leaf primordia.

Other phenotypes which occur in the most transgenic lines to different degrees of penetrance include (1) the development of adventitious meristems and/or splitting of the shoot apical meristem, (2) the production of leaves which are altered in shape or are fused, and (3) the inability of the inflorescence meristem to maintain a population of undifferentiated cells which results in the production of a terminal flower. These phenotypes support the conclusion that defects in shoot apical and inflorescence meristem formation, maintenance or function are obtained by manipulating AtRRB expression in vivo.

Transgenic lines expressing DEX-AtRRB-OE that have severe phenotypes in the uninduced condition showed an extreme phenotype when the DEX-inducible promoter was activated. Shoot and root apical meristem function was completely attenuated. Primary and secondary roots and primary leaves did not form, and the plants died with expanded but small cotyledons. This severe phenotype showed a penetrance of 100% in a population of hemizygous and homozygous individuals of two lines and slightly less in a third line. The complete loss of shoot and root meristem function in these lines following DEX induction confirms that AtRRB has a key role in meristem formation and maintenance, including control of cell cycle activity within proliferating populations of meristem cells and/or organ primordia differentiation.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. An isolated RRB polypeptide that is selected from the group of polypeptides consisting of
   a) SEQ ID NO: 2,
   b) a polypeptide encoded by a polynucleotide comprising SEQ ID NO: 1,
   c) a polypeptide encoded by a polynucleotide comprising SEQ ID NO: 9,
   d) a polypeptide encoded by a polynucleotide selected from the group of polynucleotides that hybridize under highly stringent conditions with SEQ ID NO: 1,
   e) a polypeptide encoded by a polynucleotide selected from the group of polynucleotides that hybridize under highly stringent conditions with SEQ ID NO: 9, and
   f) a polypeptide encoded by a polynucleotide selected from the group of polynucleotides that hybridize under highly stringent conditions with a polynucleotide that encodes SEQ ID NO: 2, and wherein said highly stringent hybridization conditions comprise hybridization in 40% formamide, 1 M NaCl concentration, 1% SDS at 37 deg C. and followed by at least one wash in 0.2×SSC at 60 deg C. for 20 minutes; wherein said RRB polypeptide, when expressed in a transgenic plant, causes attenuation of shoot and root apical meristem function.

* * * * *